US008762070B2

(12) United States Patent
Doyle, III et al.

(10) Patent No.: US 8,762,070 B2
(45) Date of Patent: Jun. 24, 2014

(54) SYSTEMS, DEVICES AND METHODS TO DELIVER BIOLOGICAL FACTORS OR DRUGS TO A SUBJECT

(75) Inventors: Francis J. Doyle, III, Santa Barbara, CA (US); Benyamin Grosman, Goleta, CA (US); Eyal Dassau, Goleta, CA (US); Lois Javanovic, Santa Barbara, CA (US); Howard Zisser, Santa Barbara, CA (US)

(73) Assignees: Regents of the University of California, Oakland, CA (US); Sansum Diabetes Research Institute, Santa Barbara, CA (US)

( * ) Notice: Subject to any disclaimer, the term of this patent is extended or adjusted under 35 U.S.C. 154(b) by 624 days.

(21) Appl. No.: 13/026,161

(22) Filed: Feb. 11, 2011

(65) Prior Publication Data
US 2011/0208156 A1 Aug. 25, 2011

Related U.S. Application Data

(60) Provisional application No. 61/303,555, filed on Feb. 11, 2010.

(51) Int. Cl.
*C12Q 1/54* (2006.01)
*G06F 19/00* (2011.01)

(52) U.S. Cl.
CPC .......... *G06F 19/3468* (2013.01); *G06F 19/345* (2013.01)
USPC .............................. 702/19; 604/66; 604/504

(58) Field of Classification Search
CPC ..... G06F 19/32; G06F 19/3456; G06F 19/24; G06F 19/3468; G06F 19/345
See application file for complete search history.

(56) References Cited

U.S. PATENT DOCUMENTS

| | | | |
|---|---|---|---|
| 6,544,212 B2 | 4/2003 | Galley et al. | |
| 6,595,919 B2 | 7/2003 | Berner et al. | |
| 7,806,854 B2 * | 10/2010 | Damiano et al. | 604/67 |
| 8,229,872 B2 * | 7/2012 | Gilhuly | 706/45 |
| 2003/0130616 A1 | 7/2003 | Steil et al. | |
| 2005/0171503 A1 | 8/2005 | Van Den et al. | |
| 2009/0006129 A1 * | 1/2009 | Thukral et al. | 705/2 |
| 2009/0063402 A1 | 3/2009 | Hayter | |
| 2010/0280329 A1 * | 11/2010 | Randlov et al. | 600/300 |

FOREIGN PATENT DOCUMENTS

| WO | 2005/113036 A1 | 12/2005 |
|---|---|---|
| WO | 2006124716 | * 11/2006 |

OTHER PUBLICATIONS

Bequette et al., "Automated control in biomedicine," IEEE Eng. Med. Biol. Mag. 20(1):22-3 (2001).
Bergman et al., Physiologic evaluation of factors controlling glucose tolerance in man: measurement of insulin sensitivity and beta-cell glucose sensitivity from the response to intravenous glucose. J Clin Invest. 68(6):1456-1467 (1981).
Bevier et al., "Use of continuous glucose monitoring to estimate insulin requirements in patients with type 1 diabetes mellitus during a short course of prednisone," J Diabetes Sci. Technol. 2(4):578-83 (2008).
Buckingham et al., "Prevention of Nocturnal Hypoglycemia Using Predictive Alarm Algorithms and Insulin Pump Suspension," Diabetes Care 33(5):1013-1017 (2010).
Campos-Cornejo et al., "An advisory protocol for rapid- and slow-acting insulin therapy based on a run-to-run methodology," Diabetes Technol. Ther. 12(7):555-65 (2010).
Clarke et al., "Closed-loop artificial pancreas using subcutaneous glucose sensing and insulin delivery and a model predictive control algorithm: the Virginia experience," J. Diabetes Sci. Technol. 3(5):1031-1038 (2009).
Dassau et al., "Detection of a Meal Using Continuous Glucose Monitoring," Diabetes Care 32(2):295-300 (2008).
Dassau et al., "Real-Time Hypoglycemia Prediction Suite Using Continuous Glucose Monitoring," Diabetes Care 33 (6):1249-1254 (2010).
Dassau et al., "Real-Time Hypoglycemia Prediction Suite Using Continuous Glucose Monitoring," Diabetes Care 33 (6):1249-1254 (2010)Deiss et al., "Improved glycemic control in poorly controlled patients with type 1 diabetes using real-time continuous glucose monitoring," Diabetes Care 29(12):2730-2 (2006).
Dua et al., "Model-based blood glucose control for Type 1 diabetes via parametric programming," IEEE Trans. Biomed. Eng. 53(8):1478-91 (2006).
Dua et al., "Multi-objective blood glucose control for type 1 diabetes," Med. Biol. Eng. Comput. 47(3):343-52 (2009); Epub Feb. 13, 2009.
El-Khatib et al., "A bihormonal closed-loop artificial pancreas for type 1 diabetes," Sci. Trans!. Med. 2(27):1-12 (2010).
El-Khatib et al., "A Feasibility Study of Bihormonal Closed-Loop Blood Glucose Control Using Dual Subcutaneous Infusion of Insulin and Glucagon in Ambulatory Diabetic Swine", Journal of Diabetes Science and Technology, vol. 3, Issue 4, Jul. 2009, pp. 789-803.
Ellingsen et al., "Safety constraints in an artificial pancreatic β-cell: an implementation of model predictive control with insulin on board," J. Diabetes Sci. Technol. 3(3):536-544 (2009).
Finan et al., "Experimental evaluation of a recursive model identification technique for type 1 diabetes," J Diabetes Sci. Technol. 1;3(5):1192-202 (2009).
Garg et al., "Improvement in glycemic excursions with a transcutaneous, real-time continuous glucose sensor: a randomized controlled trial," Diabetes Care 29(1):44-50 (2006).
Grosman et al., "Zone Model Predictive Control: A Strategy to Minimize Hyper- and Hypoclycemic Events," Journal of Diabetes Science and Technology 4(4):961-975 (2010).
Harvey et al., "Quest for the artificial pancreas: combining technology with treatment," IEEE Eng. Med. Biol. Mag. 29 (2):53-62 (2010).

(Continued)

*Primary Examiner* — Michael Borin
(74) *Attorney, Agent, or Firm* — Richard Aron Osam

(57) ABSTRACT

A method, computer implemented method and associated apparatus for the management of diabetes comprises utilizing zone model predictive control (Zone-MPC) to control delivery of an insulin or insulin analog within a zone of desired values.

9 Claims, 13 Drawing Sheets

(56) References Cited

OTHER PUBLICATIONS

Hovorka et al., "Nonlinear model predictive control of glucose concentration in subjects with type 1 diabetes," Physiol. Meas. 25(4):905-920 (2004).

Klonoff et al., "Continuous Glucose Monitoring: roadmap for 21st century diabetes therapy," Diabetes Care 28 (5):1231-9 (2005).

Kovatchev et al., "Quantifying temporal glucose variability in diabetes via continuous glucose monitoring: mathematical methods and clinical application," Diabetes Technol. Ther. 7(6):849-862 (2005).

Kovatchev et al., "In silico preclinical trials: a proof of concept in closed-loop control of type 1 diabetes," J. Diabetes Sci. Technol. 3(1):44-55 (2009).

Kovatchev et al., "Control to range for diabetes: functionality and modular architecture," J Diabetes Sci. Technol. 3 (5):1058-65 (2009).

Lee et al., "A Closed-Loop Artificial Pancreas Using Model Predictive Control and a Sliding Meal Size Estimator," Journal of Diabetes Science and Technology 3(5):1082-1090 (2009).

Magni et al., "Model predictive control of type 1 diabetes: an in silico trial," J. Diabetes Sci. Technol. 1(6):804-812 (2007).

Mauseth et al., "Proposed clinical application for tuning fuzzy logic controller of artificial pancreas utilizing a personalization factor," J. Diabetes Sci. Technol. 4(4):913-22 (2010).

Owens et al., "Run-to-run control of blood glucose concentrations for people with Type 1 diabetes mellitus," IEEE Trans. Biomed. Eng. 53(6):996-1005 (2006).

Palerm et al., "Robust parameter estimation in a model for glucose kinetics in type 1 diabetes subjects," Conf. Proc. IEEE Eng. Med. Biol. Soc. 1:319-22 (2006).

Palerm et al., "A Run-to-Run Control Strategy to Adjust Basal Insulin Infusion Rates in Type 1 Diabetes," J. Process Control. 18(3-4):258-265 (2008).

Paker et al., "A model-based algorithm for blood glucose control in type I diabetic patients," IEEE Trans Biomed. Eng. 46(2):148-57 (1999).

Parker et al., "The intravenous route to blood glucose control," IEEE Eng. Med. Biol. Mag. 20(1):65-73 (2001).

Parker et al., "Control-relevant modeling in drug delivery," Adv. Drug Deliv. Rev. 48(2-3):211-28 (2001).

Patek et al., "In silico preclinical trials: methodology and engineering guide to closed-loop control in type 1 diabetes mellitus," J. Diabetes Sci. Technol. 3(2):269-82 (2009).

Percival et al., "Closed-Loop Control and Advisory Mode Evaluation of an Artificial Pancreatic Beta Cell: Use of Proportional-Intergral-Derivative Equivalent Model-Based Controllers," Journal of Diabetes Science and Technology, 2 (4):636-644 (2008).

Percival et al., "Modeling the effects of subcutaneous insulin administration and carbohydrate consumption on blood glucose," J Diabetes Sci Technol. 4(5):1214-28 (2010).

Percival et al., "Development of a multi-parametric model predictive control algorithm for insulin delivery in type 1 diabetes mellitus using clinical parameters," J. Process Control 21(3):391-404 (2011).

Pfeiffer et al., "The artificial beta cell—a continuous control of blood sugar by external regulation of insulin infusion (glucose controlled insulin infusion system)," Horm. Metab. Res. 6(5):339-342 (1974).

Rabasa-Lhoret et al., "Effects of meal carbohydrate content on insulin requirements in type 1 diabetic patients treated intensively with the basal-bolus (ultralente-regular) insulin regimen," Diabetes Care 22(5):667-673 (1999).

Steil et al., "Closed-loop insulin delivery—the path to physiological glucose control," Adv. Drug Deliv. Rev. 56 (2):125-144 (2004).

Wang et al., "A Novel Adaptive Basal Therapy Based on the Value and Rate of Change of Blood Glucose," Journal of Diabetes Science and Technology 3(5):1099-1108 (2009).

Wang et al., "Automatic bolus and adaptive basal algorithm for the artificial pancreatic β-cell," Diabetes Technol. Ther. 12(11):879-87 (2010); Epub Sep. 30, 2010.

Wang et al., "Closed-loop control of artificial pancreatic Beta-cell in type 1 diabetes mellitus using model predictive iterative learning control," IEEE Trans. Biomed. Eng. 57(2):211-9 (2010); Epub Jun. 12, 2009.

Weinzimer et al., "Fully automated closed-loop insulin delivery versus semiautomated hybrid control in pediatric patients with type 1 diabetes using and artificial pancreas," Diabetes Care 31(5):934-9; Epub Feb. 5, 2008.

Zisser et al., "Basal insulin-on-board constraint in the implementation of closed-loop control," Diabetes 57(Suppl 1): A13 (2008).

Zisser et al., "Clinical update on optimal prandial insulin dosing using a refined run-to-run control algorithm," J. Diabetes Sci. Technol. 3(3):487-91 (2009).

Copenhaver, Blaine R., International Search Report and Written Opinion, PCT/US2011/024640, United States Patent and Trademark Office, May 5, 2011.

\* cited by examiner

SYSTEMS, DEVICES AND METHODS TO DELIVER BIOLOGICAL FACTORS OR DRUGS TO A SUBJECT

CROSS REFERENCE TO RELATED APPLICATIONS

The application claims priority under 35 U.S.C. §119 to U.S. Provisional Application Ser. No. 61/303,555, filed, Feb. 11, 2010, the disclosure of which is incorporated herein by reference.

STATEMENT REGARDING FEDERALLY SPONSORED RESEARCH

This invention was made with Government support under Grant No. DK085628-01 awarded by the National Institutes of Health. The Government has certain rights in this invention

TECHNICAL FIELD

The invention relates to management of drug levels or biological factors in a subject. The invention further pertains generally to management of glucose and insulin delivery levels to mimic a natural beta cell, and more particularly, to an apparatus and method for real-time control of insulin dosing and monitoring of plasma glucose levels.

BACKGROUND

Maintaining circulating levels of a drug or other biological factors in a subject is important for proper treatments and biological function.

Diabetes mellitus affects over 100 million individuals worldwide. In the US, the estimated healthcare costs of the 12 million affected is estimate to be 136 billion dollars annually. Diabetes mellitus is a disorder of the metabolism that is characterized by the inability of the pancreas to secrete sufficient amounts of insulin.

Insufficient amounts of insulin results in large fluctuations in blood glucose levels can have both short-term and long-term physiological consequences. Long-term complications arising from elevated blood glucose levels (hyperglycemia) in patients with Type 1 diabetes include retinopathy, neuropathy, nephropathy and other vascular complications. Low glucose levels (hypoglycemia) can lead to diabetic coma, seizures, accidents, anoxia, brain damage, decreased cognitive function, and death.

The conventional approach to glucose regulation in diabetic patients includes 3-5 daily insulin injections, with the quantity of insulin being determined by 4-8 invasive blood glucose measurements each day. This method of insulin delivery is painful, inconvenient and may be unreliable due to the pharmacokinetics of the insulin analogues that are typically used. Pen devices have been developed to make insulin delivery more convenient; however, the inability to mix insulin or insulin analogue types is a disadvantage. Several other routes of insulin delivery have been studied as an alternative to insulin injections including inhalation and transdermal insulin delivery. Others have explored the efficacy of continuous subcutaneous insulin infusion (CSII) using a pump. This has mainly been done in comparison to conventional insulin therapy or multiple daily insulin injections (MDI). Continuous subcutaneous insulin infusions by external insulin infusion pumps normally use rapid-acting insulin analogues.

Typical fixed dosage approaches assume that the metabolic demands of each day are metabolically similar, and that the fixed dosages adequately anticipate the timing and quantity of insulin that is required by the patient.

Unfortunately, blood glucose fluctuations continue to occur uncontrollably in many patients beyond the normal range of 70-120 mg/dl, exacerbating the risks of physical complications. Periodic episodes of hypoglycemia and hyperglycemia may occur when the insulin needs of the patient deviate from the levels predicted by regimen and present in the bloodstream.

The development of external insulin infusion pumps, along with the introduction of rapid acting insulin analogs has greatly aided in making intensive insulin therapy feasible. The efficacy of the insulin therapy is quantified by measurement of the percentage of glycosylated hemoglobin in the bloodstream (A1C). Values less than 6% are seen in normal healthy people without diabetes; whereas, higher percentages are indicative of sustained hyperglycemia.

SUMMARY

The disclosure provides an artificial pancreatic β-cell based on "Zone-MPC" that uses mapped-input data, and is automatically adjusted by linear difference personalized models. The approach described herein can also use average patient models. Control to range is, in general, applied to controlled systems that lack a specific set point with the controller goal to keep the controlled variables (CV) in a predefined zone. Control to range is highly suitable as an artificial pancreatic β-cell because of the absence of a natural glycemic set point rather than of a euglycemic zone. Moreover, using Zone-MPC leads to a reduction in control moves that will improve the energy efficiency of portable insulin pumps and will minimize oscillatory profiles of insulin delivery.

Zone-MPC was evaluated on the FDA-accepted UVa-/-U. Padova metabolic simulator. The control was based on ARX-models that were identified in a novel approach by mapping insulin and meal inputs by over-damped second-order transfer functions. The mapped inputs are used as additional state variables in the Zone-MPC formulation that enable a larger memory to the insulin administration. Zone-MPC has shown the ability to handle announced and unannounced meals with meal uncertainties. Zone-MPC showed significant advantages over the "optimal" open-loop treatment. Moreover, the Zone-MPC reduces the control moves variability with minimal loss of performance compared to set-point control. The ability to attenuate pump activity in the face of noisy continuous glucose monitoring (CGM) has been demonstrated by Zone-MPC, which will result in safer insulin delivery as well as minimize power drain. An enabling step toward a commercial product is the ability to proceed from CGM measurements directly into a functional controller in a fully automated fashion-has been demonstrated. Personalized Zone-MPC is a perfect candidate for the fully automated artificial pancreatic β-cell.

The disclosure provides a method of continuous monitoring and delivery of a drug or biological agent to a subject. The method comprises obtaining values associated with blood levels of a drug or biological agent for a subject; mapping the data using a transfer function; generating a linear difference model comprising a plurality of states; obtaining a defined value zone for the drug or biological agent in the subject; calculating a next administration dose and/or time of delivery of the drug or biological agent based on a predicted drug or biological agent value using the linear difference model and the defined zone; delivering the drug or biological agent to the subject based upon the calculated next administration. The biological agent may be a secondary (e.g., a byproduct or induced factor vs. the direct biological agent or active agent). The value can be the blood concentration of the active agent or the byproduct or a physiological symptom (e.g., temperature). In various embodiments the values are obtain in an open-loop system and may be obtained under clinical care. In one embodiment, the drug or biological agent is insulin and/or glucose. For example, in some embodiments, the value data comprises insulin and glucose levels in a subject. In yet another embodiment, the method is used to treat diabetes.

The disclosure provides a method for regulating insulin and glucose comprising obtaining insulin and meal data values and continuous glucose monitoring (CGM) data values for the subject;

mapping the insulin (I) and meal (M) data values using transfer functions:

$$I_{map}(s) = \frac{1}{(\tau_1 s + 1)(\tau_2 s + 1)} I(s)$$

$$M_{map}(s) = \frac{1}{(\tau_3 s + 1)(\tau_4 s + 1)} M(s)$$

to obtain new states $I_{map}$ and $M_{map}$, wherein $\tau$ are time points of measurement; generating a linear difference model comprising $$G_{k+1} = \alpha_1 G_k + \ldots + \alpha_p G_{k-p} +$$
$$\beta_{1_1} I_{map,k-d_1-1} + \ldots +$$
$$\beta_{1_{q_1}} I_{map,k-d_1-q_1} + \ldots +$$
$$\beta_{2_1} M_{map,k-d_2-1} + \ldots + \beta_{2_{q_2}} M_{map,k-d_2-q_2}$$

$$I_{map,k+1} = \gamma_1 I_{map,k} + \gamma_2 I_{map,k-1} + \gamma_3 I_k + \gamma_4 I_{k-1}$$

$$M_{map,k+1} = \delta_1 M_{map,k} + \delta_2 M_{map,k-1} + \delta_3 M_k + \delta_4 M_{k-1},$$

wherein $\gamma_i$ and $\delta_i$ represent weighting factors for insulin and meal, respectively, after being absorbed into the blood; obtaining a predefined glycemic zone for the subject; calculating a next insulin administration based on a predicted glycemic value using a linear difference model and a predefined glycemic zone; and delivering insulin to the subject based upon the calculated next insulin administration. In one embodiment, the delivery of insulin varies temporally and by dose. In another embodiment, the delivery of insulin is a continuous or discrete infusion. In one embodiment, the insulin is a human insulin, a mammalian insulin or an insulin analog. The glucose data can comprise episotic glucose measurements or self-monitoring measurements. The glucose measurement may be obtained subcutaneously, intravenously, intraperitoneally, or noninvasively. The CGM data is obtain from a sensor taken from the group of sensors consisting essentially of an implanted glucose sensor, an optical glucose sensor, enzymatic glucose sensor and a finger stick glucose sensor.

The administration is performed by a drug or insulin delivery pump or device. For example, a computerized implanted drug or insulin pump.

The methods of the disclosure may be implemented through a computer controlled pump or sensor. The computer may be a PDA device or other hand-held devices.

The disclosure also provides an automated pump system (e.g., an insulin pump system) comprising a controller that implements an automated method of the disclosure, wherein an insulin or insulin analog is delivered to a subject by the pump.

In some embodiments, the computer controlled or automated method is implemented via a web-based application, wireless system or other computer data transfer means.

DETAILED DESCRIPTION

Figure 1:
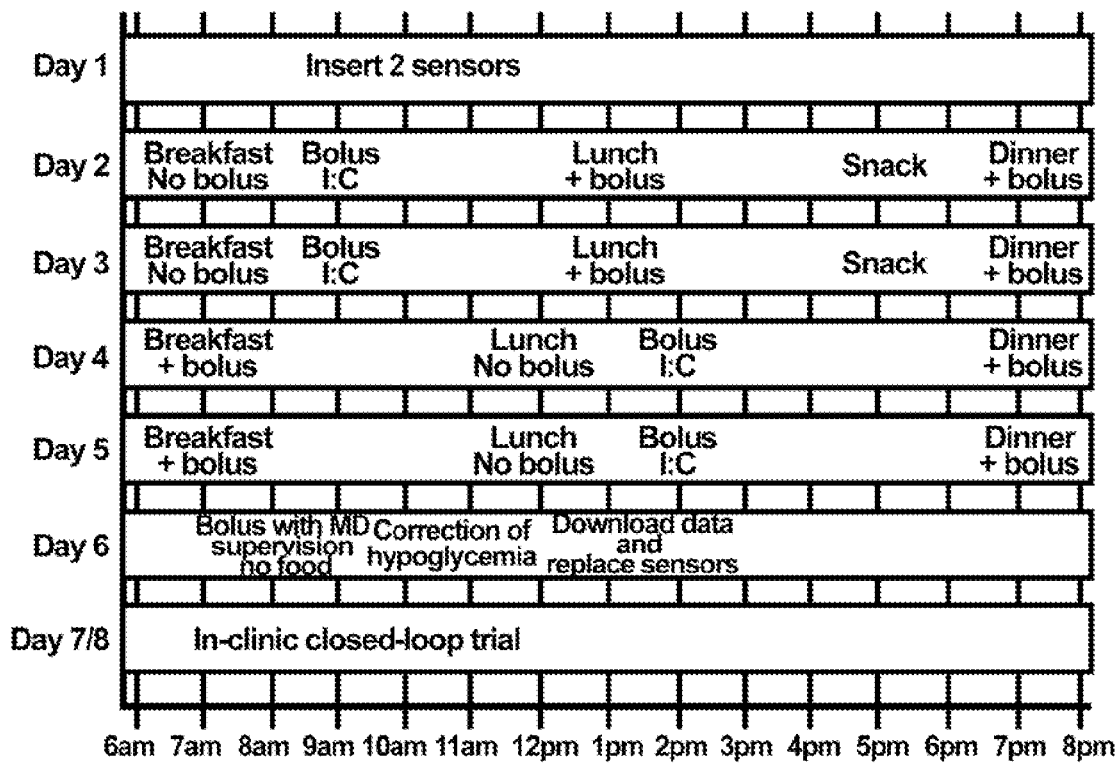
FIG. 1 shows a protocol that facilitates the separation of meal and insulin effect on blood glucose.

As used herein and in the appended claims, the singular forms "a," "and," and "the" include plural referents unless the context clearly dictates otherwise. Thus, for example, reference to "a pump" includes a plurality of such pumps and reference to "the processor" includes reference to one or more processor, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of:"

Although methods and materials similar or equivalent to those described herein can be used in the practice of the disclosed methods and compositions, the exemplary methods, devices and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

Maintaining proper circulating levels and therapeutic levels of a drug or biological factor is important in treatment of various diseases and disorders and biological function. Hormone, drug and biological factor delivery and modulation is important in homeostasis, body function and proper metabolism. Hormones (and cytokines and other biological factors) are released in response to various body functions, external stimuli, metabolic changes, and growth, to name a few.

The disclosure provides an algorithm, sampling process and delivery system that maintains drug or hormone (including cytokine and other biological factors) levels within a proper zone for proper biological activity. Although the disclosure describes, as an example, glucose and insulin, the examples are illustrative only and are not limiting. Rather, the methods, systems and devices can be used for other biological activity agents including drugs, hormones (including cytokines, and other factors) and the like. Furthermore, the methods, systems and devices can be used in the monitoring and regulation of drug delivery to maintain a desired steady state in a subject. These and other embodiments of the disclosure will be apparent in view of the description herein below.

It will be recognized that the disclosure is not limited to a particular drug or analog, but rather includes human insulin, mammalian insulin, pro-insulin, insulin analogs and the like. Similarly, drugs, prodrugs, drug analogs and the like are included in the methods of the disclosure.

The disclosure utilizes a linear difference model in combination with a model predictive control (MPC) algorithm to control drug delivery with in a zone of desired values. MPC algorithms are classified into four approaches to specify future process response: fixed set point, zone, reference trajectory, and funnel. Using a fixed set point for the future process response can lead to large input adjustments unless the controller is detuned. A zone control is designed to keep the controlled variable (CV) in a "zone" defined by upper and lower boundaries that are usually defined as soft constraints. Some MPC algorithms define a desired response path for the CVs, called reference trajectory. The reference trajectory usually describes a define path from current CV state to a desired set point. The reference trajectory control returns to a fixed set-point control when the CV approaches the defined set point. The Robust Multivariable Predictive Control Technology (RMPCT, Honeywell Inc., 1995) attempts to keep the CV in a defined zone; however, when the CV is out of the zone, a funnel is defined to bring the CV back into the zone.

Figure 2:
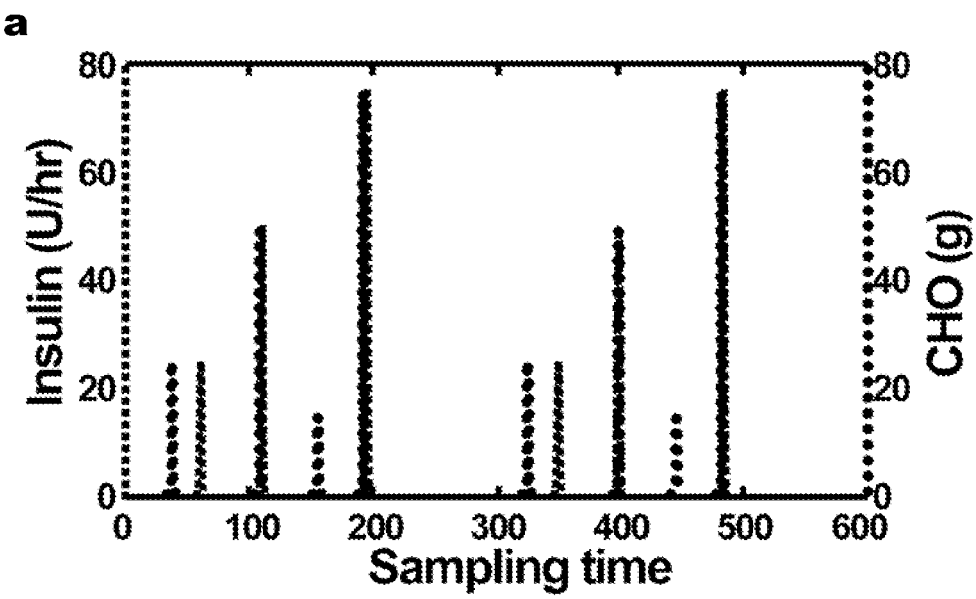
FIG. 2A-B is a plot showing insulin and meal inputs are mapped through second-order transfer functions and as a result, are spread and separated. FIG. A describes a typical input data collected from T1DM subjects: the meals and insulin are assigned as pulses over relatively close discrete time instances. FIG. B depicts the result of transformed inputs, where each pulse becomes a prolonged time response.
Figure 2:
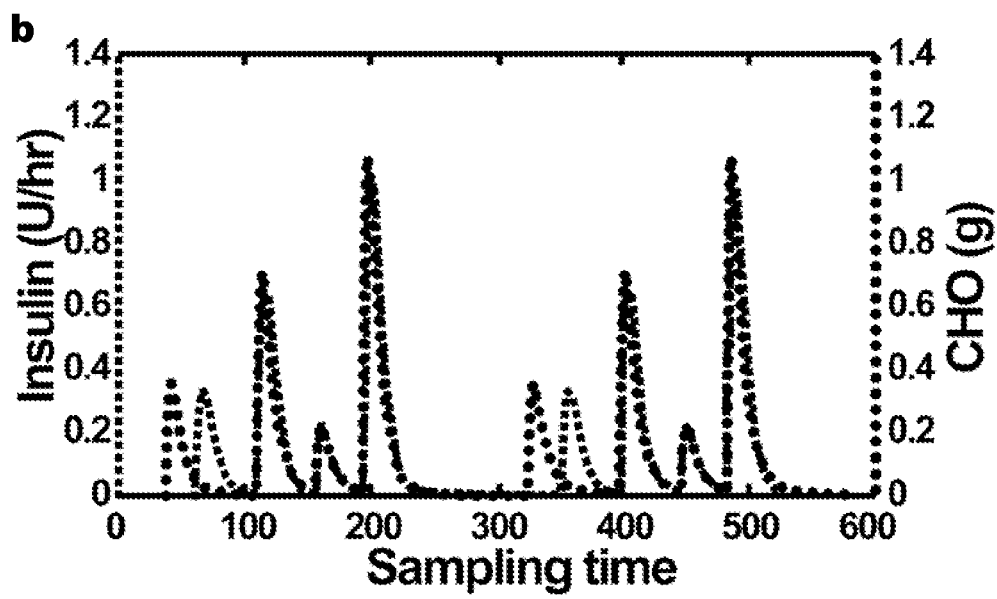
Figure 3:
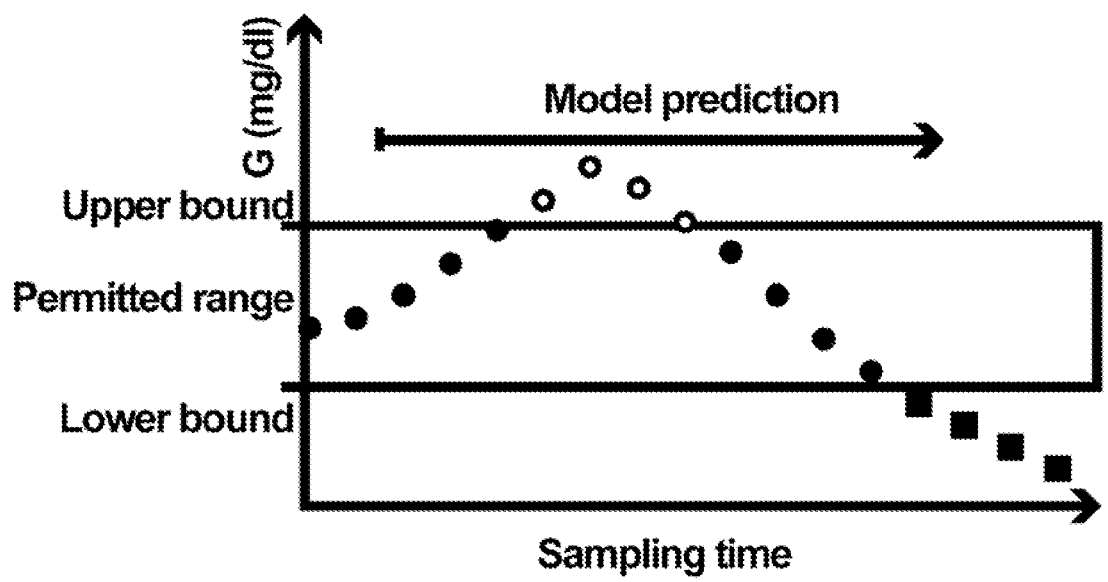
FIG. 3 is an illustration of Zone-MPC in the context of diabetes; Zone-MPC is typically divided into three different zones. The permitted range is the control target and it is defined by upper and lower bounds. For example, the green dots in the figure indicate predicted glycemic values that are in the permitted range. The upper zone represents undesirable high predicted glycemic values that are represented by orange dots in the figure. The lower zone represents undesirable low predicted glycemic values that represent hypoglycemic zone or a pre-hypoglycemic protective area that is a low alarm zone. The Zone-MPC optimizes the predicted glycemia by manipulating the insulin control moves to stay in the permitted zone under specified constrains.
Figure 4:
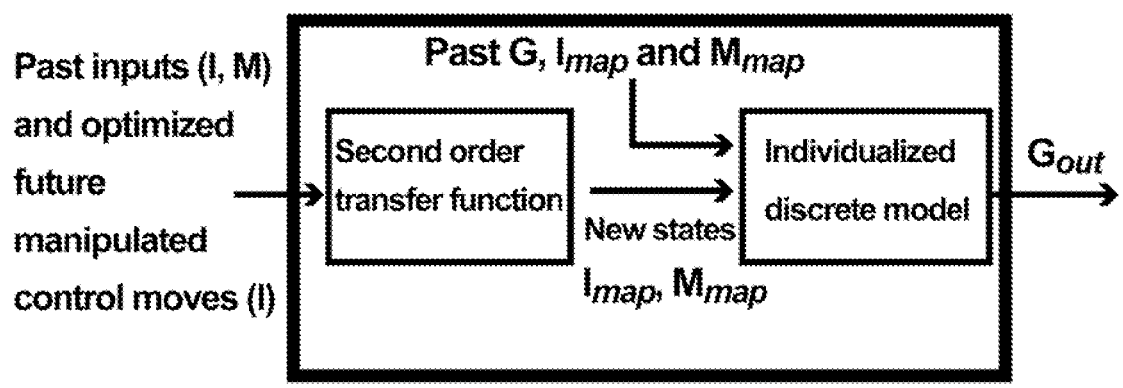
FIG. 4 shows a model prediction structure in the Zone-MPC includes two parts. First is second order transfer function that is unvaried over the different subjects. Second is an individualized discrete model that predicts the glycemia given mapped input data. The overall prediction is a result of raw data containing past outputs, inputs and future manipulated control moves that are going through the transfer functions and mapped into the new states ($I_{map}$,$M_{map}$) into the individualized discrete model to give the glycemia prediction.

Zone-MPC is applied when a CV's specific set-point value is of low relevancy compared to a zone that is defined by upper and lower boundaries. Moreover, in the presence of noise and model mismatch there is no practical value using a fixed set point. A detailed description of Zone-MPC was presented by Maciejowski. Our Zone-MPC is implemented by defining fixed upper and lower bounds (FIG. 2) as soft constrained by letting the optimization weights switch between zero and some final values when the predicted CVs are in or out of the desired zone, respectively. The predicted residuals are generally defined as the difference between the CV that is out of the desired zone and the nearest bound.

The disclosure provides an artificial pancreatic β-cell based on "Zone-MPC" that uses mapped-input data, and is automatically adjusted by linear difference personalized models. The methodology has also been extended to average patient models. Control to range is, in general, applied to controlled systems that lack a specific set point with the controller goal to keep the controlled variables (CV) in a predefined zone. Control to range is highly suitable as an artificial pancreatic β-cell because of the absence of a natural glycemic set point rather than of a euglycemic zone. Moreover, using Zone-MPC leads to a reduction in control moves that will improve the energy efficiency of portable insulin pumps and will minimize oscillatory profiles of insulin delivery.

Type 1 diabetes mellitus (T1DM) is characterized by the loss of the natural ability to produce insulin that is crucial to maintaining euglycemia and, without proper treatment with exogenous insulin injections, causes severe life-threatening complications. People with T1DM lose their ability to regulate their glycemic levels and suffer from long periods of hyperglycemia. The most common remedy offered to T1DM subjects is open-loop insulin injections; however, large numbers of subjects who are treated by open-loop injections still suffer from prolonged periods of hyperglycemia resulting in complications such as retinopathy, nephropathy, neuropathy, and vascular complications.

The development of an artificial pancreas based on an automatic closed-loop algorithm that uses a subcutaneous insulin pump and continuous glucose sensor is desirable. However, closing the loop for the artificial pancreas still presents many challenges including model identification and control.

The quest for artificial pancreatic β-cells started nearly four decades ago. These devices can be described as external or internal closed-loop systems that use continuous glucose measurements to manipulate insulin administration, and therefore compensate for the loss of natural abilities of glucoregulation of people with T1DM.

Model predictive control (MPC) is a computer control algorithm that uses an explicit process model to optimize future process response by manipulating future control moves (CM). The MPC concept was developed in the early 1970's and was referred to as identification and control (ID-COM) or as dynamic matrix control (DMC) by Shell engineers. Although MPC was originally implemented in petroleum refineries and power plants, it can be found these days in a wide variety of application areas including aerospace, food, automotive and chemical applications. The most significant of the reasons for the popularity of MPC includes its handling of constraints, it accommodation of nonlinearities, and its ability to formulate unique performance criteria.

MPC optimizes every control cycle with a cost function that includes P future process instants, known as prediction horizon, and M future control moves (CM), the control horizon. In each cycle, the optimization is repeated using updated process data. However, only the first control move of each optimized sequence is sent to the process. Process inputs and outputs constraints are included directly such that the optimum solution prevents future constraint violation.

Model predictive control (MPC) is a promising algorithm for controlling substance delivery to a subject (e.g., an artificial pancreas control algorithm). MPC is an optimal control algorithm that has been used in the chemical process industries over the last four decades. MPC is based upon repeated open-loop optimizations that minimize a cost function by using model-based predictions.

The process of developing the algorithm includes developing based levels and predicted levels. Measurements of biological materials in the clinic can be used to develop various baseline and values for developing the algorithm. In one embodiment, clinical data, usually include discrete information about insulin delivery and meals, is used to generate personalized models. Mapping clinical insulin administration and meal history through two different second-order transfer functions improves the identification accuracy of these models. Moreover, using mapped insulin as an additional state in Zone-MPC enriches the information about past control moves and thereby reduces the probability of over-dosing.

The disclosure provides a drug/biological factor injection process and systems referred to as "Zone-MPC" that uses mapped-input data, and is automatically adjusted by linear difference personalized models for modulating and injecting a biological substance including a hormone, cytokine, drug, or other factor. Control to range is, in general, applied to controlled systems that lack a specific set point with the controller goal to keep the controlled variables (CV) in a predefined zone.

In one embodiment, the disclosure provides an artificial pancreatic β-cell based on "Zone-MPC" that uses mapped-input data, and is automatically adjusted by linear difference personalized models. Control to range is, in general, applied to controlled systems that lack a specific set point with the controller goal to keep the controlled variables (CV) in a predefined zone. Control to range is highly suitable as an artificial pancreatic β-cell because of the absence of a natural glycemic set point rather than of a euglycemic zone. Moreover, using Zone-MPC leads to a reduction in control moves that will improve the energy efficiency of portable insulin pumps.

Figure 10:
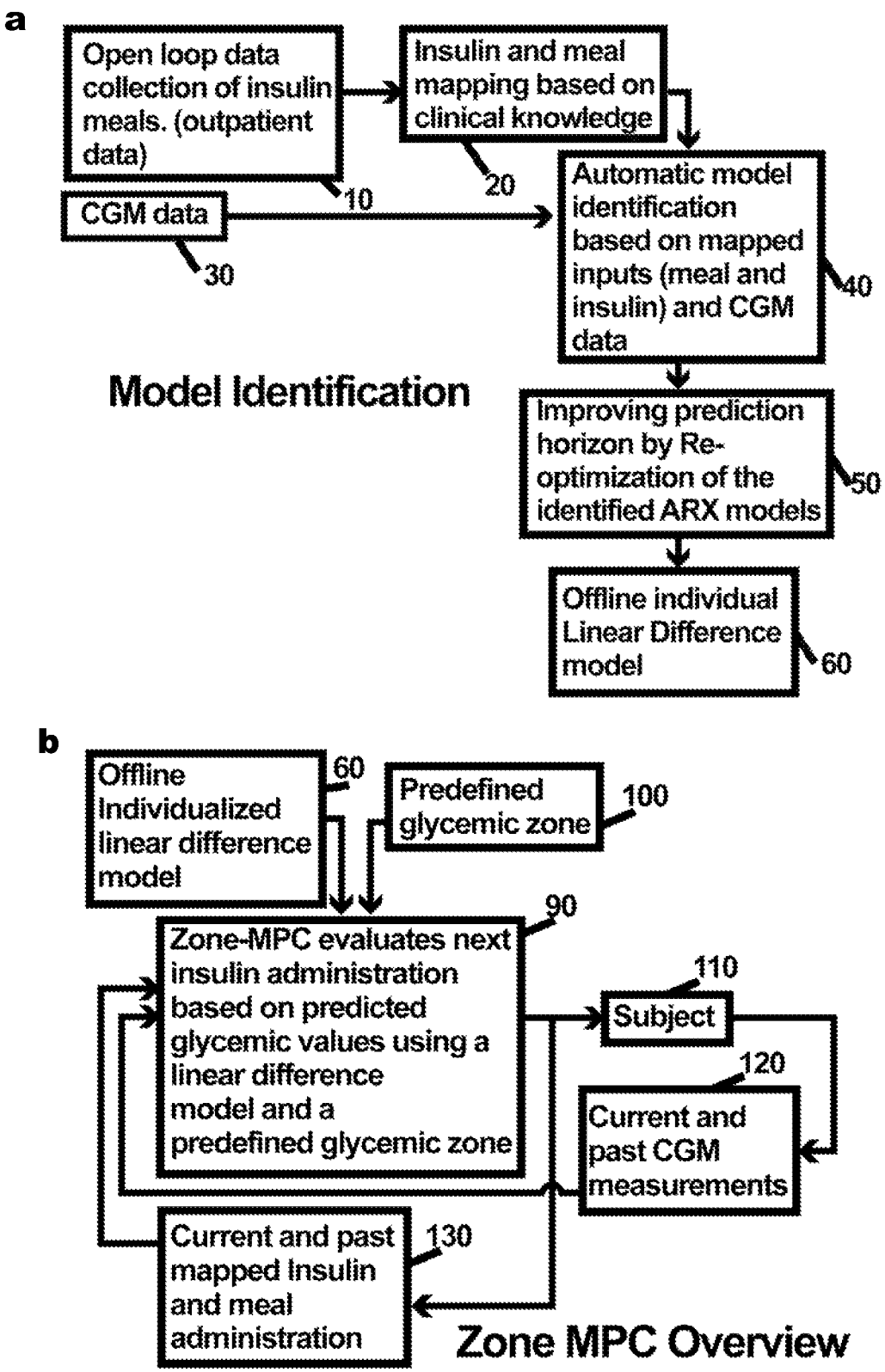
FIG. 10A-C shows various flow charts of embodiments of the disclosure.
Figure 10:
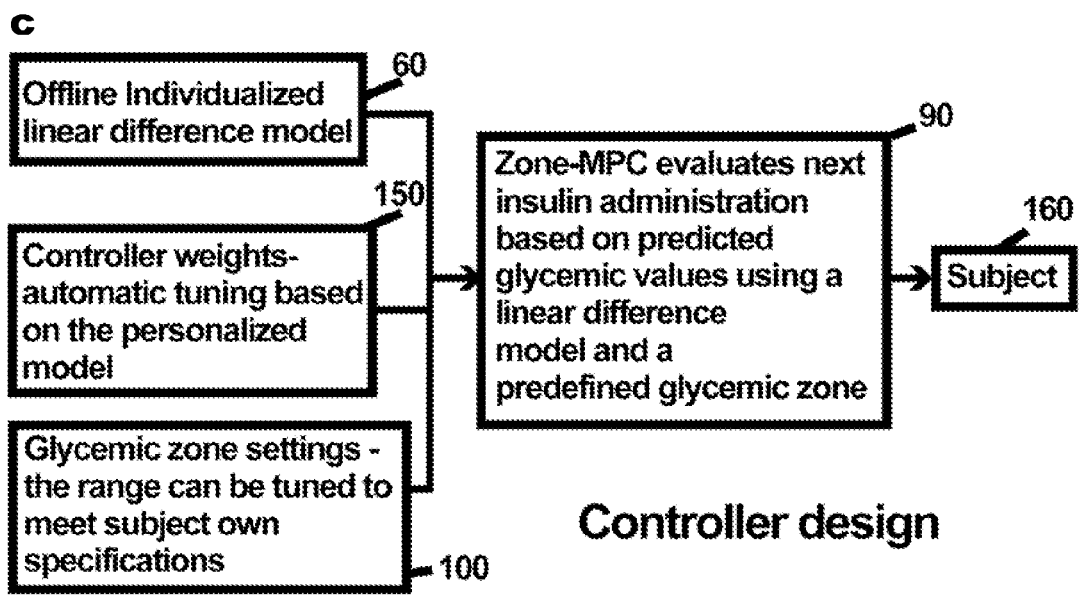

Referring to FIG. 10, a flow chart of embodiments of the disclosure is depicted. The flow charts are directed to glucose and insulin, however, it will be recognized that other drugs, hormones and the like may be similarly processed in the methods and systems of the disclosure. As shown in box 10, open loop data collection of insulin meals is obtained. The data can be obtained by feeding a subject followed by bolus injection of insulin. The obtained data is then used to map insulin meal levels (box 20). As shown in box 30, continuous glucose blood measurements are obtained. Such levels can be detected using any number of glucose sensors. An automatic model identification formula is then identified (from a plurality of different autoregression exogenous (ARX) input models) based upon the measured and mapped insulin meals and glucose measurements (box 40). The model then may be further improved by re-optimization of the autoregression exogenous input model (box 50). This optimized autoregression exogenous input model is the used as an individualized linear difference model (box 60) which may comprise a plurality of linear states.

The obtained linear difference model (box 60) is then used to support the evaluation and determination of the next drug/factor delivery time and dose (box 90) in combination with a predefined clinical dose zone (see, e.g., FIG. 10B, box 100). As used herein a "dose zone" comprises a lower limit blood concentration and an upperlimit blood concentration of a particular biological agent. In other embodiments of the disclosure, alternative physiological variables can be controlled to a "zone", including blood pressure, oxygen saturation, lactate, and temperature using methods of the disclosure. In the case of glucose, the dose zone or "glycemic zone" comprises the upper and lower level of the targeted glucose concentration in the blood. The methods and systems of the disclosure are used to keep the biological factor (e.g., glucose) within the "zone". As depicted in FIG. 10, box 110, insulin, for example, is delivered to the subject, followed by a glucose measurement and an evaluation of both current and past insulin, meal and glucose levels (boxes 120 and 130). This information is fed back into the Zone-MPC process algorithm (box 90) and the cycle repeats.

A slightly different depiction of the process is depicted in FIG. 10C. In this depiction the linear difference model (box 60) in combination with controller weights (box 150) and zone settings (box 100) are fed into the Zone-MPC algorithm (box 90) to determine the dose and timing of the next biological agent delivery (e.g., delivery of a drug, hormone such as insulin and the like) to the subject (box 160).

As depicted in the flow charts, Zone-MPC model is based on linear difference equations that are initiated by an autoregression with exogenous input (ARX) model that is selected by its prediction competency and then re-optimized to improve its prediction abilities. The ARX model that serves as the basis for a linear difference equation predictor for the Zone-MPC is chosen from a catalog of ARX-model candidates. The different ARX-models are scored by their prediction competencies over a fixed horizon and the ARX-model that scores the higher prediction $R^2$, equation (1), over a fixed horizon is then re-optimized to give a new linear difference equation that will be the Zone-MPC predictor.

Equation (1) presents the $R^2$ index, where $y \in R^N$ is a vector of collected data points, $\bar{y}$ is the mean of the collected data points, and $\hat{y} \in R^N$ is the predicted value. The $R^2$ index approaches 1 for perfect model predictions and 0 for models that do not predict better than a constant mean value.

$$R^2 = 1 - \frac{\sum_{k=1}^{n}(y(k)-\hat{y}(k))^2}{\sum_{k=1}^{n}(y(k)-\bar{y})^2} \qquad (1)$$

Linear difference equations use past input/output discrete records to generate a future discrete prediction. For example, Equation (2) describes the connection between the predicted output y at instant k and the past p and q output and input records, respectively.

$$\hat{y}(k) = \alpha_1 y(k-1) + \ldots + \alpha_p y(k-p) + \beta_1 u(k-1) + \ldots + \beta_q u(k-q) \hat{y}(k) = \phi \cdot \theta^T \quad (2)$$

where $$\phi = [y(k-1) \ldots y(k-p) u(k-1) \ldots u(k-q)]$$

and $$\theta = [\alpha_1 \ldots \alpha_p \beta_1 \ldots \beta_q]$$

In the presence of observed data $\underline{y} \in R^N$, where N are the number of collected data points, a linear regression can be performed to establish the regression vector $\theta$ values by minimizing the sum squares of errors between the N data records $\underline{y}$ and predicted values $\underline{\hat{y}}$ as it is formulated in equation (3).

$$\min_\theta \left\{ \frac{1}{N} \sum_{k=1}^{N} (y(k) - \phi \cdot \theta^T)^2 \right\} \quad (3)$$

The regression on the past output regressors, $[\alpha_1 \ldots \alpha_p]$, is defined as auto-regression, and the model is referred to as an ARX model.

The determination of the ARX-model output order, input order and delay, is subject to data validation and complexity considerations. ARX model identification is initialized by the researcher's decision based upon reasonable orders and delays. A pool of ARX models are then generated by the different combinatory combinations of orders and delays, and each ARX-model is appraised by its prediction abilities on calibration data and typically on validation data. Some tradeoff can be formulated between model prediction abilities and the ARX-model complexity, for example, the Akaike information criterion (AIC). However, the quality of the collected data for identification will eventually govern the identification.

In order to best simulate an in vivo experiment, a data collecting protocol was applied to the FDA-accepted UVa-/-U.Podava metabolic simulator. In the data-collecting protocol (FIG. 1), no adjustments to daily routine are prescribed in day one. Both days two and three start at 7 am with a 25 g carbohydrate (CHO) breakfast with no insulin bolus, followed by a correction bolus at 9 am; at 1 pm a 50 g CHO lunch is taken together with a correction bolus. A 15 g CHO snack without a correction bolus is given at 5 pm, and a 75 g CHO dinner without bolus is given at 8 pm. Day four and five start at 7 am with a 25 g CHO breakfast accompanied by an insulin bolus, then a 50 g lunch is consumed at 12 pm, and an insulin bolus is given at 2 pm. At 8 pm a 75 g CHO dinner without insulin bolus is given and at 10 pm an insulin bolus is administered. On the sixth day the response to a pure bolus from fasting conditions is tested by bolus administration at 9 am.

The data of meal and insulin inputs are mapped through second-order transfer functions (Equation (4)) to overcome an identification problems: a large gain uncertainty is caused by the opposite effects of meal and insulin that are frequently delivered in close time instants. Losing the ability to distinguish between meal and insulin gains can produce poor models for control. However, mapping the input data using two different second-order transfer functions (FIG. 2) separates and spreads the input data, providing better terms to regress for the model. Clinical observations and pharmacokinetic/pharmacodynamic data suggest that, on average, the effect of insulin on blood glucose is observed 30 minutes after injection, and that the effect of meals on blood glucose is observed after 20 minutes. This a priori knowledge has been used to design the following second-order transfer functions:

$$I_{map}(s) = \frac{1}{(\tau_1 s + 1)(\tau_2 s + 1)} I(s) \quad (4)$$

$$M_{map}(s) = \frac{1}{(\tau_3 s + 1)(\tau_4 s + 1)} M(s)$$

$$I_{map}(s) = \frac{1}{(30s + 1)(25s + 1)} I(s) \quad (4a)$$

$$M_{map}(s) = \frac{1}{(10s + 1)(45s + 1)} M(s)$$

Equation (4) describes the transfer functions used to map the measured insulin and meal, I and M respectively into new states $I_{map}$ and $M_{map}$. $\tau_{1-4}$ represents time constants 1-4 respectively. Equation 4a shows a similar model in which the time constants have been set to 30 minutes, 25 minutes, 10 minutes and 45 minutes.

The ARX-model regressors are normally set by a one step shift of the output/input data, such that each prediction at time instant k is evaluated by the recorded output/input data until time instant k−1. However, the predicted output at instant k is highly correlated to the output measurement at instant k−1, especially when the sampling time is relatively short. This can lead to ARX-models that lose their predictive capabilities.

An addition in the suggested identification procedure is tuning the ARX regressors using horizon prediction optimization. Horizon prediction optimization minimizes the recursive prediction over a defined prediction horizon (PH). Horizon prediction optimization uses the overall sequences of predicted values, starting at a one step prediction, and containing the overall prediction till PH steps after. This differ other generic optimizations that usually use solely the values after PH sampling times. The horizon prediction optimization cost function (Equation (6)) attempts to minimize the normalized-sum-squares-of-errors (SSE) between the output recorded data, y and the recursive prediction, $y_{rec}$. In the horizon prediction optimization, unlike in the linear regression that is performed in common ARX modeling, the value of vector $y_{rec}$ is updated after each PH cycle. The value of the predicted $\hat{y}_{rec}$ at instant k is a function of past predictions k−1 until p, where p is the order of the auto-regressors. The past values of $\hat{y}_{rec}$ are set to be equal to the past values of y after each recursive prediction to the length of PH. The result is a set of recursive prediction segments that cover the length of abs(N/PH)·PH, where N is the number of data records. The initial condition for the horizon prediction optimization is the one-step-ahead ARX-model solution, which can be generated instantly. Moreover, constraints are applied to the new linear difference equation that results from the horizon prediction optimization. The following five constraints are applied to the optimization to prevent models from being unstable, having non-physical gains, or having inverse responses and so that they may be suitable for the predictive control:

1. For stability, the roots of the following of the characteristic polynomial, $z^p - \alpha_1 z^{p-1} - \alpha_2 z^{p-2} \ldots - \alpha_p$, are all inside the unit circle, where $[\alpha_1 \alpha_2 \ldots -\alpha_p]$ are the auto regressors.

2. Negative insulin gain requirement, $$\frac{\sum_{i=1}^{q_1} \beta_i}{1 - \sum_{j=1}^{P} \alpha_j} < 0,$$

where $[\beta_1 \beta_2 \ldots -\beta_p]$ are the insulin regressors.

3. Positive meal gain requirement, $$\frac{\sum_{i=1}^{q_2} \gamma_i}{1 - \sum_{j=1}^{P} \alpha_j} > 0,$$

where $[\gamma_1 \gamma_2 \ldots -\gamma_p]$ are the meal regressors.

4. No inverse response in insulin, $\text{sign}([\beta_1 \ldots \beta_{q_1}])=0$, where $\text{sign}(\overline{x})$ is defined by Equation (1).

5. No inverse response in meal, $\text{sign}([\gamma_1 \ldots \gamma_{q_2}])=0$.

$$\text{sign}(\overline{x}) = \begin{cases} 0 & \forall \overline{x} \in \quad \text{one side of the origin} \\ 1 & \exists [x_i, x_j] \quad \text{on both sides of the origin} \end{cases} \quad (1)$$

Equation (5) describes a Boolean function that results in 0 if provided with a vector that has elements on only one side of the origin (i.e., all positive or all negative). The function results in 1 if provided with a vector that has at least two elements from different sides of the origin.

Equation (6) describes the cost function V of the horizon prediction optimization, where $y_{data}(k)$ is the data record at instant k, $y_{rec}(k)$ is the recursive prediction at instant k. $I_{map}$ and $M_{map}$ are the mapped insulin and meal data records, respectively. p, $q_1$, and $q_2$ are the order of the output (glycemia), insulin, and meal respectively, and $d_1$ and $d_2$ are the insulin and meal delays in sampling time, respectively. $\alpha_k$, $\beta_k$, and $\gamma_k$ are the regressors of the glucose, insulin, and meal, respectively.

$$V = \min_{\theta} \left\{ \frac{\sum_{d=1}^{\downarrow(N/PH)} \sum_{k=(d-1)PH+1}^{PH \cdot d} (y_k - y_{rec,k})^2}{\sum_{i=1}^{N} (y_i - \overline{y})^2} \right\} \quad (6)$$

where $$y_{rec} = \begin{cases} y & \mod(k, PH) = 0 \\ \phi \cdot \theta^T & \mod(k, PH) \neq 0 \end{cases}$$

where $$\phi = [y_{rec,k-1} \ldots y_{rec,k-p} \; I_{map,k-d_1-1} \ldots I_{map,k-d_1-q_1} \; M_{map,k-d_2-1} \ldots M_{map,k-d_2-q_2}]$$

$$\theta = [\alpha_1 \ldots \alpha_p \; \beta_1 \ldots \beta_{q_1} \; \gamma_1 \ldots \gamma_{q_2}]$$

s.t.

$$\text{roots}\{z^P - \alpha_1 z^{P-1} - \alpha_2 z^{P-2} \ldots - \alpha_p\} < 1$$

-continued $$\frac{\sum_{i=1}^{q_1} \beta_i}{1 - \sum_{j=1}^{P} \alpha_j} < 0 \quad (7)$$

$$\frac{\sum_{i=1}^{q_2} \gamma_i}{1 - \sum_{j=1}^{P} \alpha_j} > 0$$

$$\text{sign}([\beta_1 \ldots \beta_{q_1}]) = 0$$

$$\text{sign}([\gamma_1 \ldots \gamma_{q_2}]) = 0$$

$$J(u) = \sum_{j=1}^{P} \|(y_{k+j} - y^r_{k+j})\|Q_j + \sum_{j=0}^{M-1} \|(u_{k+j} - u_s)\|R_j + \|\Delta u_{k+j}\|S_j$$

s.t.

$$x_{k+j} = f(x_{k+j-1}, u_{k+j-1}) \forall \; j = 1, P$$

$$y_{k+j} = g(x_{k+j}, u_{k+j}) \forall \; j = 1, P$$

$$u_{min} \leq u_{k+j} \leq u_{max} \forall \; j = 1, M$$

$$\Delta u_{low} \leq \Delta u_{k+j} \leq \Delta u_{up} \forall \; j = 1, M$$

Equation (7) describes a typical objective function used in the MPC format engaging three contributions: future output trajectory ($y_{k+j}$) deviation from desired output trajectory ($y_{k+j}^r$) over a prediction horizon P; future input ($u_{k+j}$) deviation from nominal value $u_s$ over control horizon M; and control moves increments ($\Delta u_{k+j}$) over control horizon M. The relative share of each of the four components of the objective function is managed by the time dependent weight matrices $Q_j$, $S_j$, and $R_j$. The optimization is conducted under model constraints ($x_{k+j}$, are the model state variables), upon constraints on maximum and minimum nominal input values ($u_{min}$ and $U_{max}$), and on minimum and maximum control moves increments ($\Delta u_{low}$ and $\Delta u_{up}$). The solution of the optimization using the objective function described by Equation (7) is the vector $u \in R^M$.

The different $\overline{\text{MPC}}$ algorithms can be classified into four approaches to specify future process response: fixed set point, zone, reference trajectory, and funnel. Using a fixed set point for the future process response can lead to large input adjustments unless the controller is detuned. A zone control is designed to keep the controlled variable (CV) in a zone defined by upper and lower boundaries that are usually defined as soft constraints. Some MPC algorithms define a desired response path for the CVs, called reference trajectory. The reference trajectory usually describes a define path from current CV state to a desired set point. The reference trajectory control returns to a fixed set-point control when the CV approaches the defined set point. The Robust Multivariable Predictive Control Technology (RMPCT, Honeywell Inc., 1995) attempts to keep the CV in a defined zone; however, when the CV is out of the zone, a funnel is defined to bring the CV back into the zone.

Zone-MPC is applied when a CV's specific set-point value is of low relevancy compared to a zone that is defined by upper and lower boundaries. Moreover, in the presence of noise and model mismatch there is no practical value using a fixed set point. A detailed description of Zone-MPC was presented by Maciejowski. Our Zone-MPC is implemented by defining fixed upper and lower bounds (FIG. 2) as soft constrained by letting the optimization weights switch between zero and some final values when the predicted CVs are in or out of the desired zone, respectively. The predicted residuals are generally defined as the difference between the CV that is out of the desired zone and the nearest bound.

The core of Zone-MPC dwells in its cost function formulation that holds the zone consideration. Zone-MPC, like any other forms of MPC, predicts the future $\hat{y} \in R^P$ output by an explicit model using past m input/output records and future input $\hat{u} \in R^M$ moves that need to be optimized. However, instead of driving to a specific fixed set point, the optimization attempts to keep or move the predicted outputs into a zone that is defined by upper and lower bounds.

Figure depicts Zone-MPC applied to glycemia regulation. Fixed upper and lower glycemic bounds are pre-defined. Using a linear difference model the glycemic dynamics are predicted and the optimization reduces future glycemic excursions from the zone under constraints and weights defined in its cost function.

The Zone-MPC cost function used in the present examples is defined as follows:

$$J(\underline{u}) = \sum_{j=1}^{P} \|y_{k+j}^{range}\|Q + \sum_{j=0}^{M-1} \|(u_{k+j} - u_s)\|R \quad (8)$$

s.t.

$$y_{k+j} = f(y_{k+j-1}, u_{k+j-1}) \; \forall \; j = 1, P$$

$$0 \le u_{k+j} \le u_{max} \; \forall \; j = 1, M$$

where Q and R are constant optimization weights upon the predicted outputs and the future inputs, respectively, and $\underline{y}^{range}$ is a superposition of all the predicted outputs states that exceed the permitted range:

$$y_{k+j}^{range} = [y_{k+j}^{lower}\text{-lower bound}, y_{k+j}^{upper}\text{-upper bound}] \quad (9)$$

$\underline{y}_{lower} \in R^P$ collects all the predicted points that are below the lower bound by setting all other predicted values to zero:

$$\underline{y}_{lower} = \sum_{j=1}^{P} y_{k+j} \cdot C_j^1 \quad (10)$$

where $$C_j^1 = \begin{cases} 1 & y_{k+j} < \text{lower bound } j = 1, P \\ 0 & y_{k+j} \ge \text{lower bound } j = 1, P \end{cases}$$

$\underline{y}_{upper} \in R^P$ collects all the predicted points that are above the upper bound by setting all other predicted values to zero:

$$\underline{y}_{upper} = \sum_{j=1}^{P} y_{k+j} \cdot C_j^2 \quad (11)$$

where $$C_j^2 = \begin{cases} 1 & \forall \; y_{k+j} > \text{upper bound } j = 1, P \\ 0 & \forall \; y_{k+j} \le \text{upper bound } j = 1, P \end{cases}$$

The future CMs are hard constrained set by the insulin pump's ability to deliver a maximum rate of insulin and the inability to deliver negative insulin values. The objective function (equation (8)) neglects the control move increments component to enable fast control movements.

The second-order input transfer functions described by equation (4) are used again to generate an artificial input memory in the Zone-MPC schema to prevent insulin overdosing, and as a result hypoglycemia. In order to avoid over delivery of insulin, the evaluation of any sequential insulin delivery must take into consideration the past administered insulin against the length of the insulin action. However, a one-state linear difference model with a relative low order uses the output (glycemia) as the main source of past administered input (insulin) "memory." In the face of model mismatch, noise, or change in the subject's insulin sensitivity, this may result in under or over-delivery of insulin. This can be mitigated by adding two additional states for the mapped insulin and meal inputs.

As was discussed earlier the ARX-models were identified using mapped inputs. The insulin and meal measurements and the transfer functions that were used for the identification can be embedded into one ARX-model with one state (glucose) and two inputs (insulin and meal) as described in equation (12).

$$G_{k+1} = \alpha_1 G_k + \ldots + \alpha_p G_{k-p} + \beta_{11} I_{k-d_1-1} + \ldots + \quad (12)$$
$$\beta_{1q_1} I_{k-d_1-q_1} + \ldots + \beta_{21} M_{k-d_2-1} + \ldots + \beta_{2q_2} M_{k-d_2-q_2}$$

where, G, I, and M represent glucose blood concentration, insulin administration, and meals, respectively. $\alpha_i$, $\beta_{1i}$, and $\beta_{2i}$ are model coefficients, $d_1$ and $d_2$ are insulin and meal time delays, respectively, and P, $q_1$, and $q_2$ are the orders of glucose, insulin, and meal, respectively.

In order to generate a prediction using equation (12) P past measurements are needed of G and $d_1+q_1$ and $d_2+q_2$ past insulin and meal measurements respectively. However, while G has infinite memory that is the outcome of the deterministic difference equation the inputs memory is restricted to the past inputs of a restricted order. For example, if delay in insulin, $d_1$, is equal to two sample times and the order of insulin in the model is equal to three sample times then the model captured the insulin administration of only five previous sample times. In perfect conditions where there is no model mismatch, no noise or change in insulin sensitivity, the past inputs will be contained into the G dynamics; however, in reality, these conditions are unlikely to be achieved.

An alternative formulation of the model, which provides a full reliable input memory to the system, is described in equation (13).

$$G_{k+1} = \alpha_1 G_k + \ldots + \alpha_p G_{k-p} +$$
$$\beta_{11} I_{map,k-d_1-1} + \ldots +$$
$$\beta_{1q_1} I_{map,k-d_1-q_1} + \ldots +$$
$$\beta_{21} M_{map,k-d_2-1} + \ldots + \beta_{2q_2} M_{map,k-d_2-q_2}$$

$$I_{map,k+1} = \gamma_1 I_{map,k} + \gamma_2 I_{map,k-1} + \gamma_3 I_k + \gamma_4 I_{k-1}$$

$$M_{map,k+1} = \delta_1 M_{map,k} + \delta_2 M_{map,k-1} + \delta_3 M_k + \delta_4 M_{k-1} \quad (13)$$

where $I_{map}$ and $M_{map}$ are the new states representing the mapped insulin and meal values respectively. $\gamma_i$ and $\delta_i$ are new addition to the set of coefficients. These new states represent the insulin and meal after being absorbed into the blood.

Equation (13) describes an improved formulation to Equation (12) that uses the mapped insulin and meal inputs ($I_{map}$ and $M_{map}$ respectively) as additional states. The two new states are evaluated using the two past new states records as well as two past input records. Keeping the past new states records enable an infinite input memory that is independent to the G measurements. The states are updated after each Zone-MPC cycle and there by maintain the influence of all past inputs.

Four main tuning parameters are available for MPC. First, the prediction horizon, P, is a fixed integer indicating the number of prediction samples that will be used by the MPC cost function. P should be on the order of the settling time. Choosing P that is too small will cause the loss of valuable dynamic response. On the other hand, choosing P that is too large will reduce the influence of dynamics over steady-state. Second, the control horizon, M, is an integer indicative of the control moves that are optimized. A large M will create a sluggish control response; however, choosing M=1 will cause highly aggressive control. The other two parameters are Q and R, as described earlier. When applying Zone-MPC, in addition to the four MPC tuning parameters, the zone can be treated as another tuning variable.

The most dominant dynamic property found to influence the Zone-MPC tuning was the ARX-model's settling time (ST). The settling time is defined as the time it takes for a dynamic system to accomplish 95% of a response to a step input. The prediction horizon P was set to correspond to the individual subject model ST. However, when the ratio between P and M is changed (equation (8)), then the relative cost between the output and the input deviations is changed as well.

It should be noted that glucose predictions based on ARX models are limited to approximately three hours. Hence, to correctly compensate for prolonged settling-times, the weight upon the control moves (R) is a function of the ST. In this way the balance between the weights of the output and input is conserved in Equation (8). Moreover, the model fitness based upon three hours prediction is used as additional penalty upon R.

$$R = \frac{ST}{(FIT_{over\ three\ hours})^{1.5}} \quad (14)$$

Equation (14) describes the adjusted cost weight upon the control moves. ST is defined by sampling times and $FIT_{over\ three\ hours}$ is assumed to have a value greater than zero and lower than one and was calculated by Equation (15).

$$FIT_{over\ three\ hours} = 1 - \frac{\sum_{k=p+1}^{N-PH} y_{over\ three\ hours,k} - y_k}{\sum_{j=p+1}^{N-PH} y_j - \bar{y}} \quad (15)$$

where $y_{over\ three\ hours} \in R^{N-(p+PH)}$ is a vector containing the collection of the ARX model predictions over three hours, PH is the number of sampling times contained in three hours, p is the order of the auto-regressors. N is the total number of data values, $y_{data} \gamma R^N$ is the vector of the data values, and $\bar{y}_{data}$ is the mean of the data values.

Q and M were used as fixed values of 1 and 5 respectively.

Zone-MPC succeeds in maintaining glycemic responses closer to euglycemia, compared to the "optimal" open-loop treatment in the three different modes with and without meal announcement. In the face of meal uncertainty, announced Zone-MPC presented only marginally improved results over unannounced Zone-MPC. When considering user error in CHO estimation and the need to interact with the system, unannounced Zone-MPC is an appealing alternative. Zone-MPC reduces the variability of the control moves over fixed set-point control without the need to detune the controller. This gives the Zone-MPC the ability to act quickly when needed and reduce unnecessary control moves in the euglycemic range.

Nine control experiments are conducted on ten in silico adult subjects following a three meal scenario of 75, 75 and 50 grams of CHO at 7 am, 1 pm and 8 pm, respectively using the FDA-accepted UVa-/-U.Padova metabolic simulator. In all MPC experiments the weight upon predicted outputs, Q, is set to 1, while the weight upon the future control moves, R, is set automatically by equation (14).

Zone-MPC was tested in three different modes using unannounced and announced meals in their nominal value and with 40% uncertainty. Ten adult in silico subjects were evaluated following a scenario of 75, 75, and 50 grams of carbohydrates (CHO) consumed at 7 am, 1 pm and 8 pm respectively. Zone-MPC results are compared to those of the "optimal" open-loop pre-adjusted treatment. Nine experiments were conducted as follows:

Experiment 1: Built-in open-loop pre-adjusted treatment is applied with nominal meals value.

Experiment 2: Zone-MPC bounds are set between 80 and 140 mg/dL and the meals are unannounced.

Experiment 3: Zone-MPC bounds are set between 100 and 120 mg/dL and the meals are unannounced.

Experiment 4: MPC with set point at 110 mg/dL and meals are unannounced.

Experiment 5: Zone-MPC bounds are set between 80 and 140 mg/dL and the nominal meals are announced.

Experiment 6: Zone-MPC bounds are set between 100 and 120 mg/dL and the nominal meals are announced.

Experiment 7: MPC with set point at 110 mg/dL and the nominal meals are announced.

Experiment 8: Built-in open-loop pre-adjusted treatment is tested with meals announced with −40% mismatches with the consumed meals value.

Experiment 9: Zone-MPC bounds are set between 80 and 140 mg/dL with meals announced with −40% mismatches with the consumed meals value.

Figure 5:
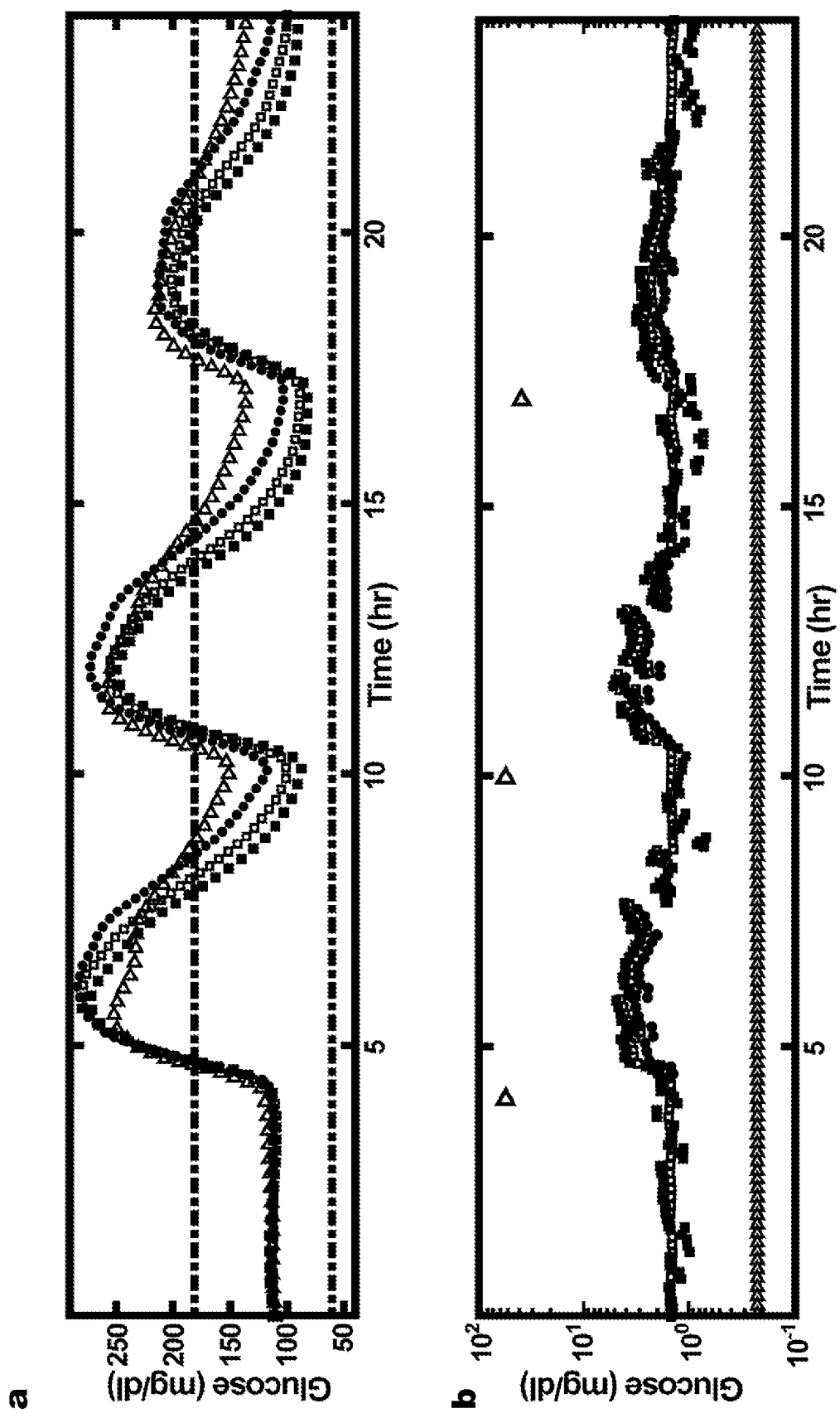
FIG. 5 is a comparison between experiments 1 to 4 as applied to UVa subject #5. Experiments 1 to 4 are represented by grey triangles and red, blue and black circles, respectively. Figures (a) and (b) depict the glycemic response and the insulin administration, respectively. The dashed black line indicates on 60 and 180 [mg/dL]. The insulin administration is presented in semi-logarithmic scale to include the open-loop bolus treatment, and the controller insulin administrations, in a single plot.

FIG. 5 describes a test that was conducted on subject #5 of the UVa simulator. In FIG. 5, experiments 1 to 4 are represented by grey triangles and red, blue, and black circles, respectively. FIG. 5 shows that the tighter the range of the Zone-MPC is, the more variable the control moves become. In FIG. 5, experiment 1 shows some advantage over the MPC experiments on the first meal; however, this advantage is a result of the test initialization that is overruled through the rest of the test.

Figure 6:
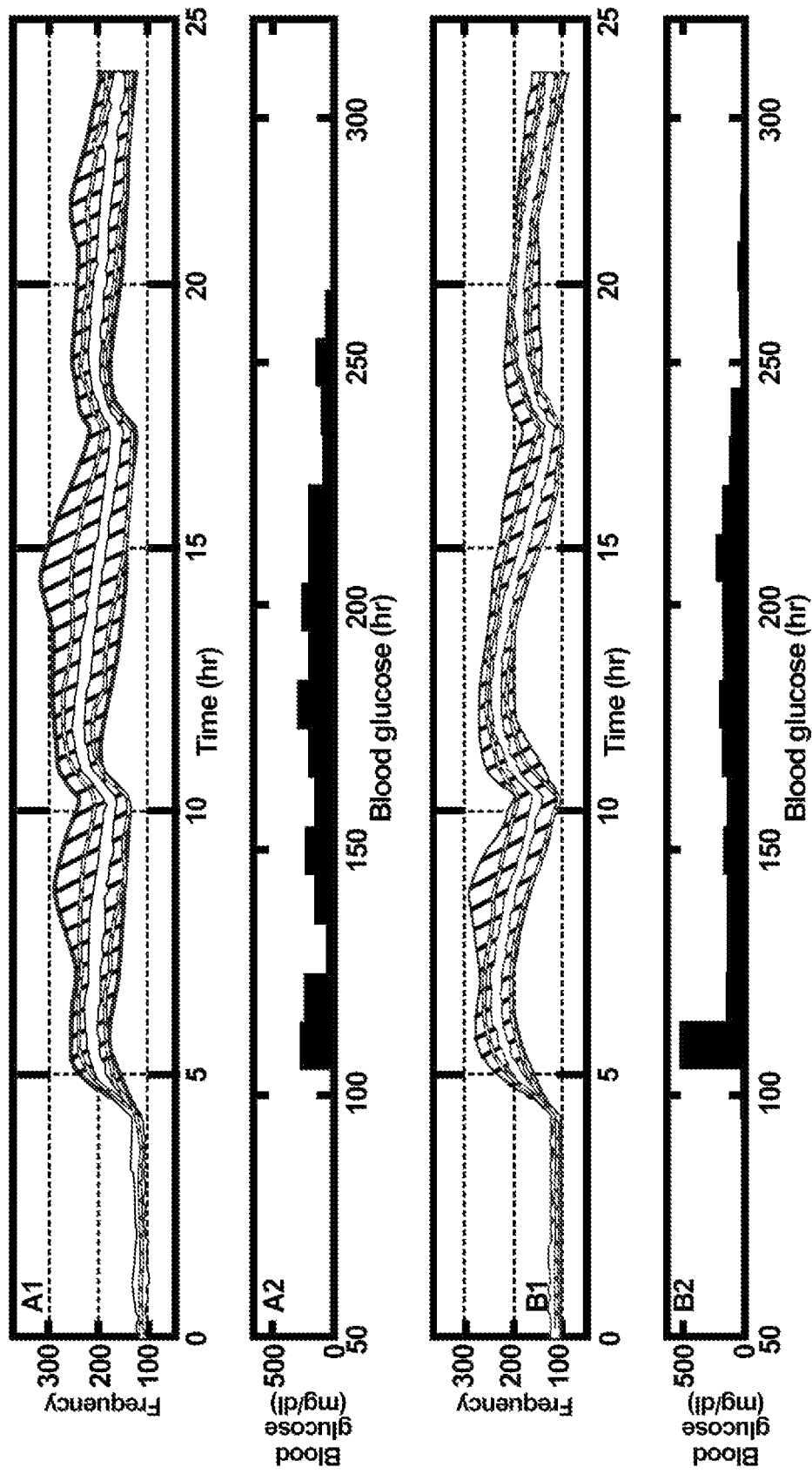
FIG. 6 shows the population result of experiments 1 to 4, (a) to (d), respectively, on ten UVa-/-U.Padova subjects. The grey area bounds are the minimum and maximum points at each given time instant, the green solid line is the mean glycemic response and the dashed red lines are the mean glycemic standard deviation envelope at each time instant. Glucose distribution for experiments 1 to 4 is presented in the histogram plots.
Figure 6:
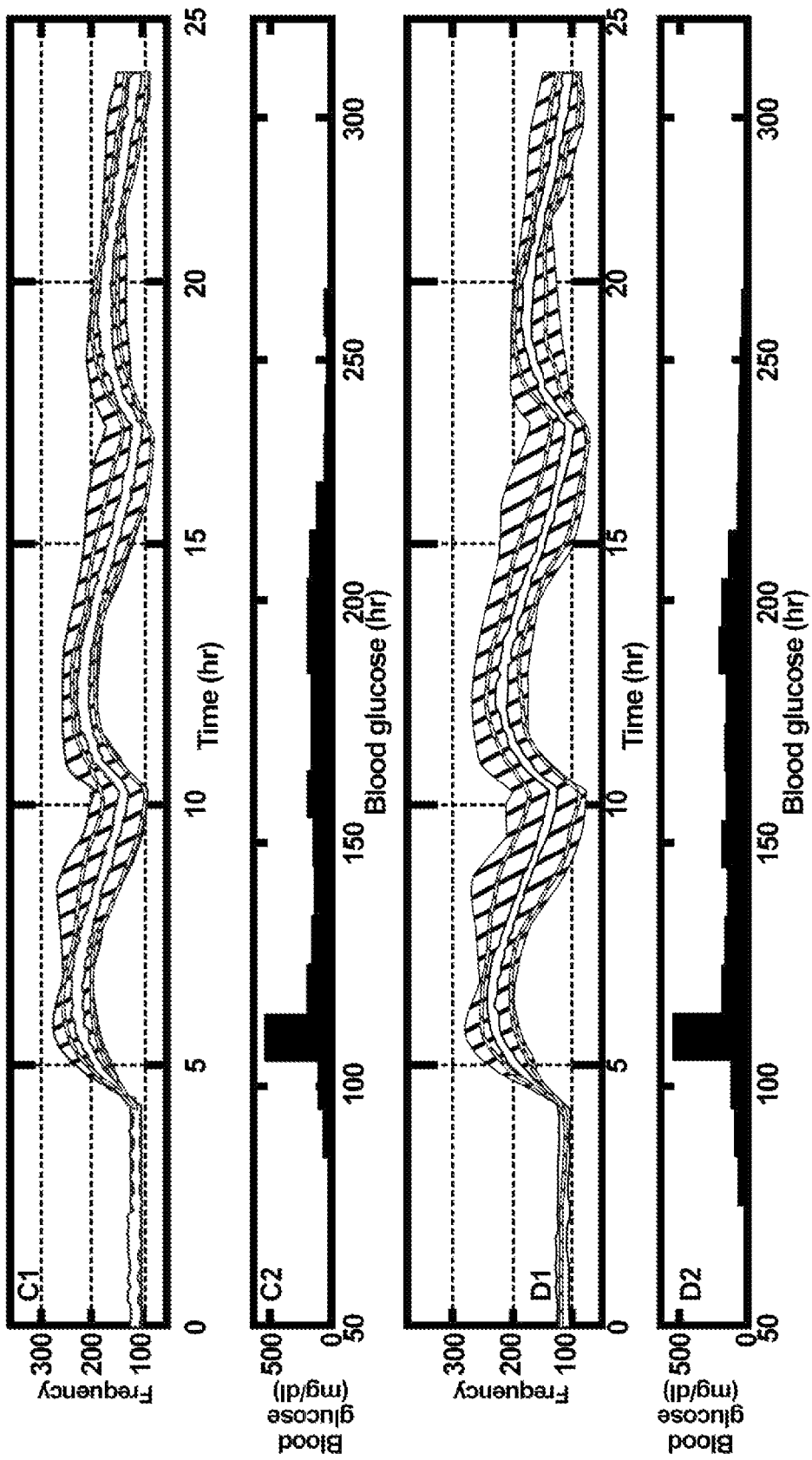

FIG. 6 presents a population result of experiments 1 to 4, (a) to (d) respectively, on all 10 UVa-/-U.Padova subjects. Experiment 1, 2, 3, and 4 mean glucose values are 180, 171, 160, and 155 mg/dL with average standard deviations (STD) of 27, 22, 23, and 23 mg/dL reaching the maximum values of 314, 291, 280, and 274 mg/dL and the minimum values of 110, 85, 83, and 76 mg/dL, respectively. Experiment 1 shows the highest mean, STD, and maximum value, which indicate on inferiority of the "optimal" open-loop treatment. For experiments 2 to 4, the minimum and maximum values decrease as the range becomes narrower. However, the STD of experiment 2 is the lowest, which implies a decrease in the control performance variability between the ten subjects and which indicates higher reliability.

Figure 7:
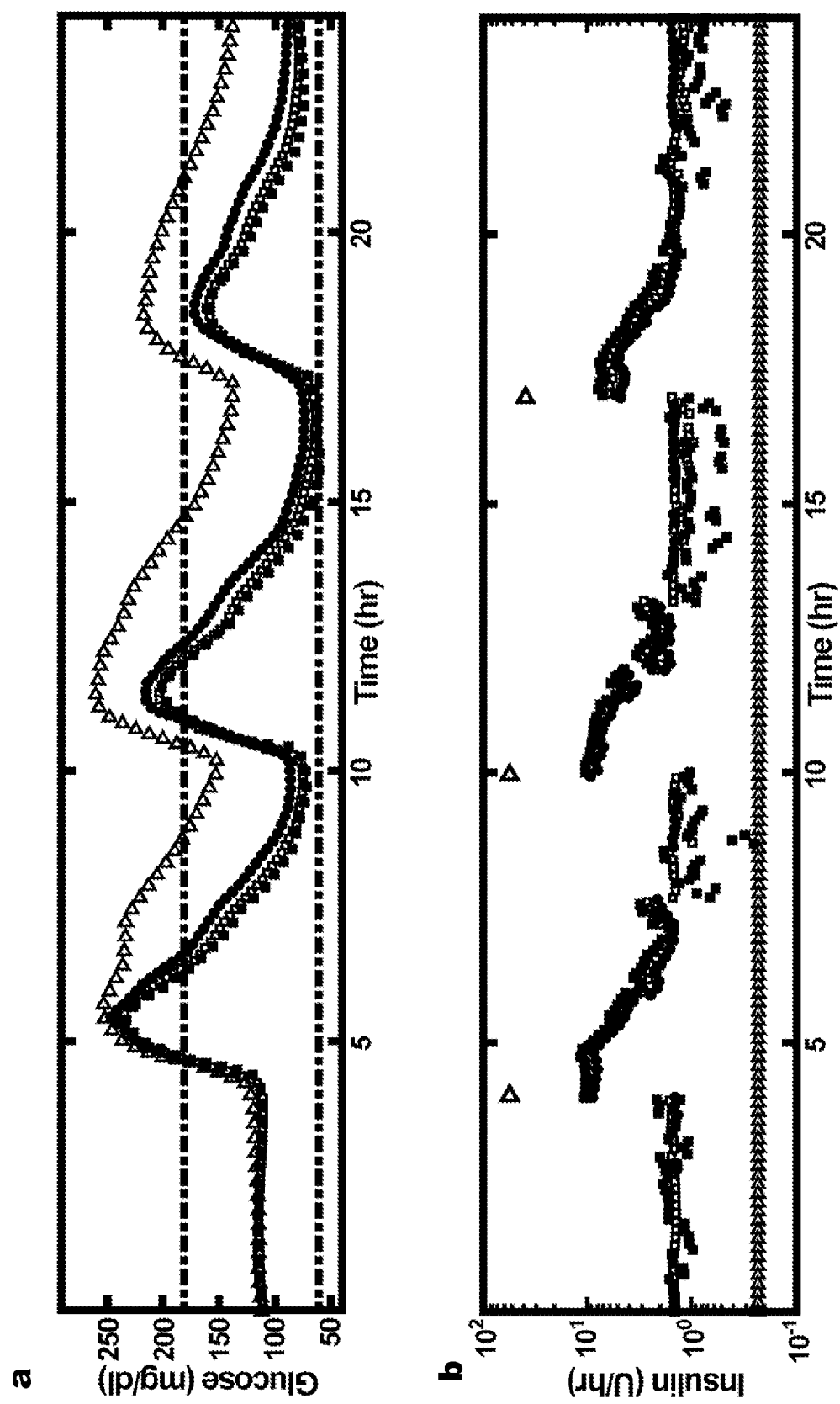
FIG. 7 shows a comparison between experiments 1, 5, 6 and 7 when applied to UVa subject #5. Experiments 1, 5, 6 and 7 are represented by grey triangles and red, blue and black circles, respectively. Figures (a) and (b) depict the glycemic response and the insulin administration, respectively. The insulin administration is presented in semi-logarithmic scale to include the open-loop bolus treatment, and the controller insulin administrations, in a single plot.

FIG. 7 shows a comparison between experiments 1, 5, 6, and 7 on subject #5 of the UVa-/-U. Padova metabolic simulator and are indicated by grey triangles, and red, blue and black circles, respectively. As was shown in 7, the narrower the range of the Zone-MPC, the more variable the control signal become. When announcement of meals is implemented (experiments 5, 6 and 7), Zone-MPC presents superior regulation over the open-loop treatment throughout the day by a faster meal disturbance rejection.

Figure 8:
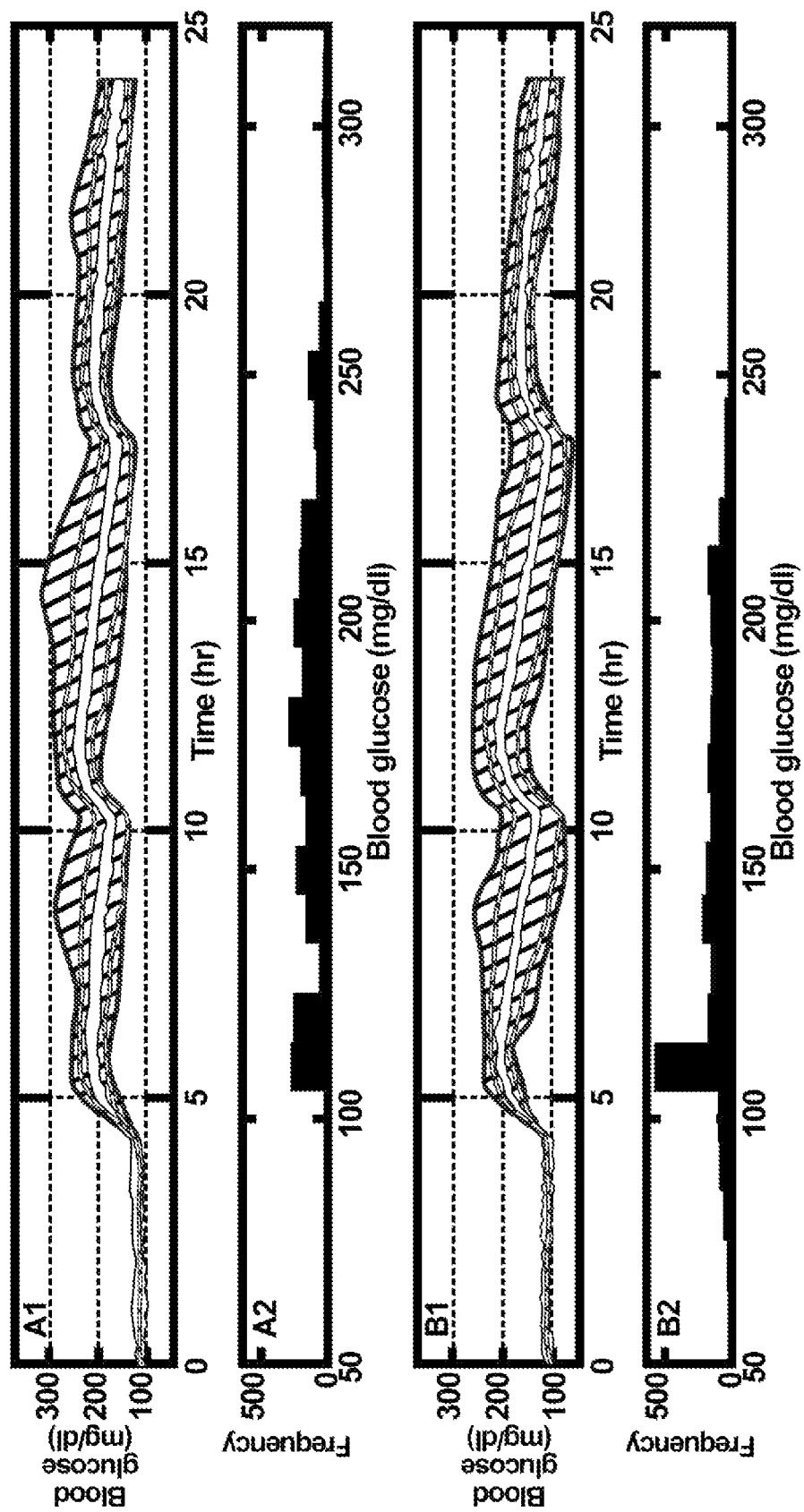
FIG. 8 shows population result of experiments 1, 5, 6, and 7 on 10 UVa-/-U.Padova subjects. The grey area bounds are the minimum and maximum points at each given time instant, the green solid line is the mean glycemic response and the dashed red lines are the mean glycemic standard deviation envelope at each time instant. Glucose distribution for experiments 1 5, 6, and 7 is presented in the histogram plots.
Figure 8:
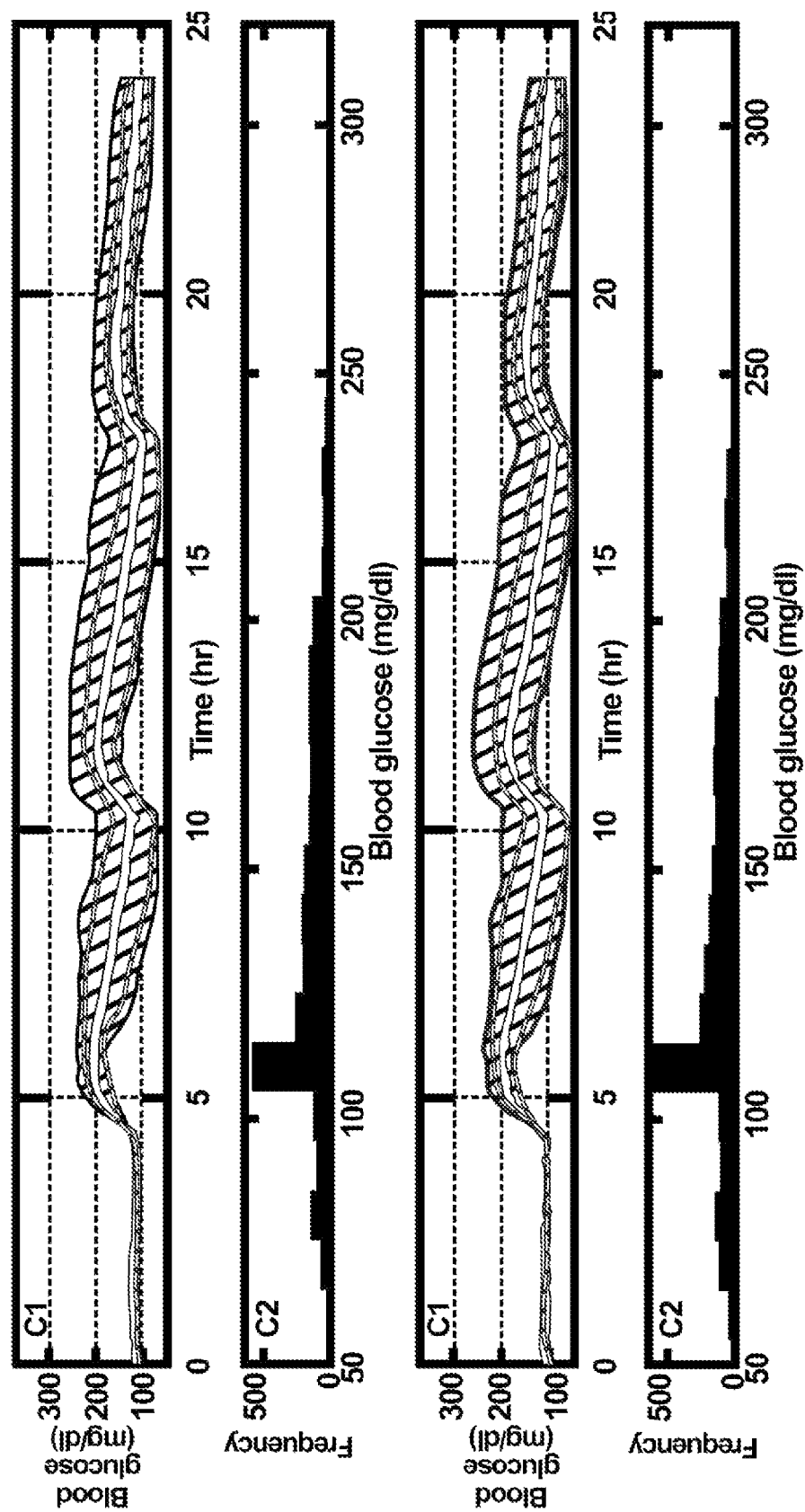

FIG. 8 presents a population result of experiments 1, 5, 6, and 7, (a) to (d), respectively, on all ten UVa-/-U.Padova subjects. Experiment 1, 5, 6, and 7 mean glucose values are 180, 152, 141, and 136 mg/dL with an average STD of 27, 28, 29, and 29 mg/dL reaching the maximum values of 314, 267, 262, and 258 mg/dL and the minimum values of 110, 66, 62, and 59 mg/dL, respectively. It can be seen that the result of announced meals are the reduction of mean, maximum and minimum values. However, reducing the minimum values also increase the likelihood of hypoglycemic events especially for experiment 7.

Figure 9:
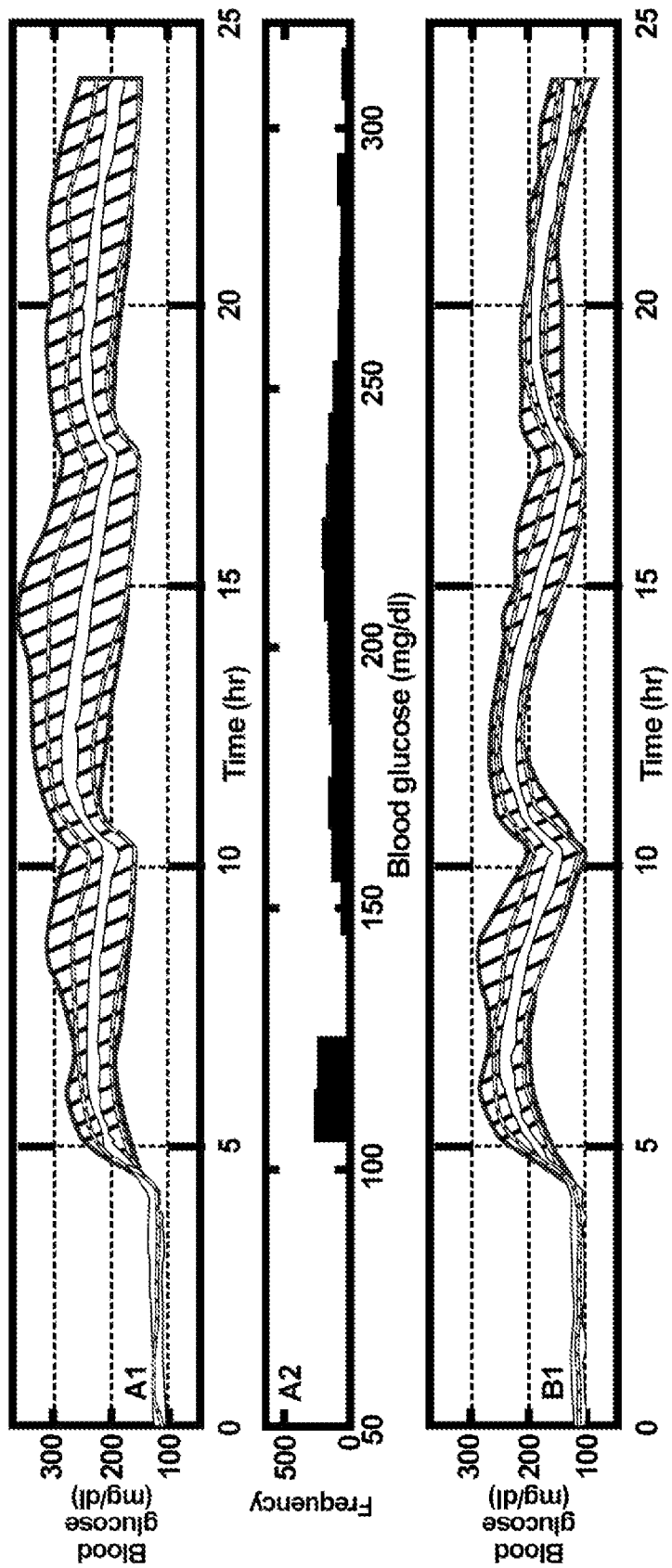
FIG. 9 is a population result of experiments 2, 8, and 9 on 10 UVa-/-U.Padova subjects. The grey area bounds are the minimum and maximum points at each given time instant, the green line is the mean glycemic response and the dashed red lines are the mean glycemic ±STD at each time instant. Glucose distribution for experiments 2, 8, and 9 is presented in the histogram plots.
Figure 9:
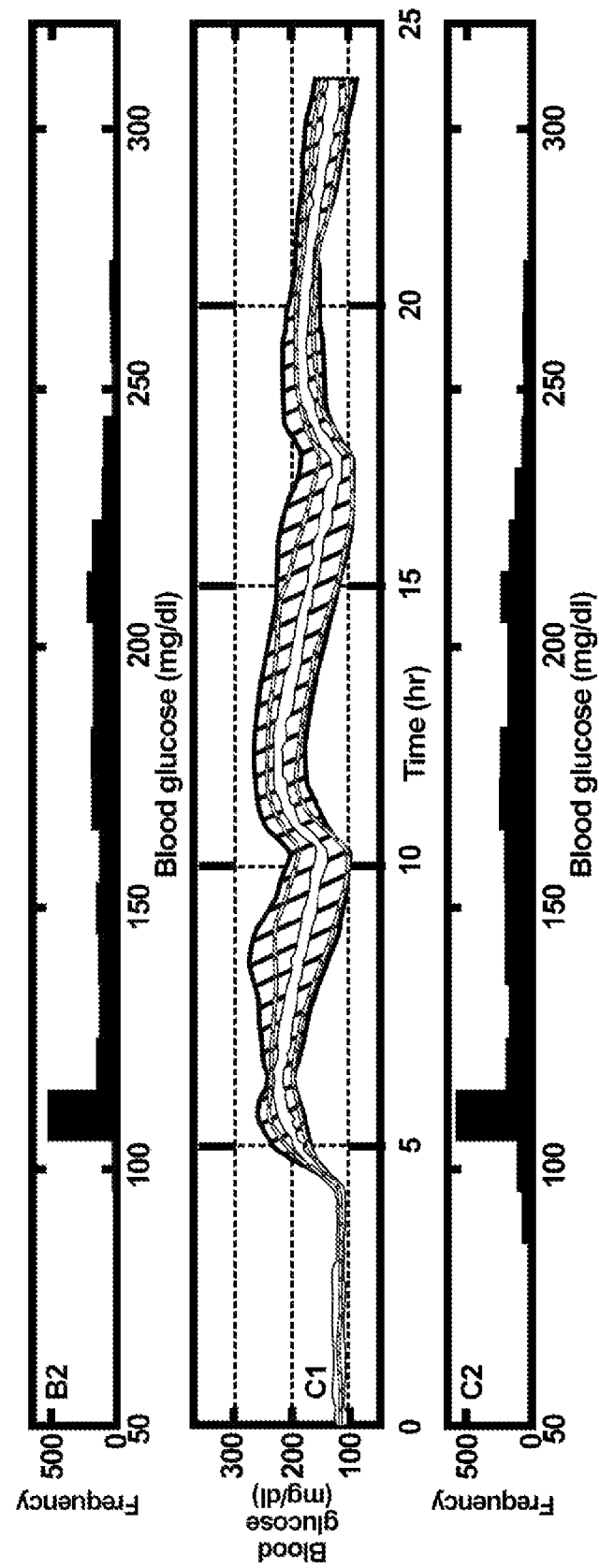

FIG. 9 describes the population responses on the ten UVa-/-U. Padova subjects using experiments 2, 8, and 9. Experiment 2, 8, and 9 mean glucose values are 171, 205, and 161 mg/dL with an average STD of 22, 36, and 24 mg/dL reaching the maximum values of 291, 364, and 274 mg/dL and the minimum values of 85, 110, and 85 mg/dL, respectively. Experiment 8 shows the obvious disadvantage of using open-loop treatment in the face of uncertainties. Experiment 8 results in extended hyperglycemic with extreme glucose values over 300 mg/dL. Comparing experiment 2 and 9, the advantages of the meal announcement decreases in face of uncertainties, and the two experiments reach similar performance indices.

pared to set-point control. Furthermore, the ability to attenuate pump activity in the face of noisy continuous glucose monitoring (CGM) has been demonstrated by Zone-MPC, which results in safer insulin delivery as well as minimize power drain. Personalized Zone-MPC is a perfect candidate for the fully automated artificial pancreatic β-cell or other drug or hormone delivery systems.

Zone-MPC is applied when a fixed set point is not fully defined and the control variable objective can be expressed as a zone. Because euglycemia is usually defined as a range, Zone-MPC is a control strategy for the artificial pancreatic β-cell.

In one embodiment, an apparatus/device of the disclosure includes a data communication interface, one or more processors operatively coupled to the data communication interface, a memory for storing instructions which, when executed by the one or more processors, causes the one or more processors to receive a data from an infusion device and an analyte monitoring device process the information utilizing a Zone-MPC method described herein and delivery a biological agent (e.g., insulin) to a subject. Moreover, one or more storage devices having processor readable code embodied thereon can be used including, for example, PDAs (e.g., iPHONEs, or other Bluetooth capable devices.

The various processes described above including the processes performed by the delivery device, the controller unit

TABLE 1

Table 1. Results summary of time spent over 180 mg/dL ($TO_{180}$[min]) and number of hypoglycemic events ($HYPO_\#$ [—]) for ten subjects in all nine experiments.

| Subject # | | Exp# 1 | Exp# 2 | Exp# 3 | Exp# 4 | Exp# 5 | Exp# 6 | Exp# 7 | Exp# 8 | Exp# 9 |
|---|---|---|---|---|---|---|---|---|---|---|
| 1 | $TO_{180}$ | 1107 | 1074 | 970 | 938 | 1006 | 947 | 919 | 1156 | 1018 |
|   | $Hypo_\#$ | 0 | 0 | 0 | 0 | 0 | 0 | 0 | 0 | 0 |
| 2 | $TO_{180}$ | 993 | 587 | 412 | 221 | 487 | 189 | 156 | 1115 | 540 |
|   | $Hypo_\#$ | 0 | 0 | 0 | 0 | 0 | 0 | 0 | 0 | 0 |
| 3 | $TO_{180}$ | 657 | 486 | 471 | 456 | 455 | 434 | 417 | 730 | 470 |
|   | $Hypo_\#$ | 0 | 0 | 0 | 0 | 0 | 0 | 0 | 0 | 0 |
| 4 | $TO_{180}$ | 1140 | 587 | 480 | 466 | 57 | 0 | 0 | 1147 | 155 |
|   | $Hypo_\#$ | 0 | 0 | 0 | 0 | 0 | 0 | 0 | 0 | 0 |
| 5 | $TO_{180}$ | 708 | 635 | 538 | 485 | 208 | 171 | 160 | 889 | 405 |
|   | $Hypo_\#$ | 0 | 0 | 0 | 0 | 0 | 0 | 1 | 0 | 0 |
| 6 | $TO_{180}$ | 1149 | 766 | 596 | 520 | 635 | 417 | 259 | 1150 | 711 |
|   | $Hypo_\#$ | 0 | 0 | 0 | 0 | 0 | 0 | 0 | 0 | 0 |
| 7 | $TO_{180}$ | 413 | 428 | 309 | 291 | 73 | 56 | 58 | 739 | 195 |
|   | $Hypo_\#$ | 0 | 0 | 0 | 0 | 0 | 0 | 0 | 0 | 0 |
| 8 | $TO_{180}$ | 457 | 855 | 585 | 523 | 612 | 475 | 349 | 1098 | 743 |
|   | $Hypo_\#$ | 0 | 0 | 0 | 0 | 0 | 0 | 0 | 0 | 0 |
| 9 | $TO_{180}$ | 153 | 385 | 319 | 269 | 265 | 181 | 120 | 477 | 324 |
|   | $Hypo_\#$ | 0 | 0 | 0 | 0 | 0 | 0 | 0 | 0 | 0 |
| 10 | $TO_{180}$ | 492 | 596 | 444 | 421 | 233 | 119 | 88 | 885 | 423 |
|    | $Hypo_\#$ | 0 | 0 | 0 | 0 | 0 | 0 | 0 | 0 | 0 |

As noted, Exp#8 (Experiment # 8, open loop with 40%) meal uncertainty, shows the highest time over 180 mg/dL in minutes for all ten subjects. Subject # 5 experience a single hypoglycemic event following experiment 7 (Exp#7). Exp # 7 also presents the minimal duration over 180 mg/dL for all subjects.

Zone-MPC as described herein was evaluated on the FDA-accepted UVa-/-U. Padova metabolic simulator. The control was based on ARX-models that were identified in a novel approach by mapping insulin and meal inputs by overdamped second-order transfer functions (it will be recognized that mapped biological factors, other than insulin may be used similarly). The mapped inputs are used as additional state variables in the Zone-MPC formulation that enable a larger memory to the insulin administration.

Zone-MPC has shown the ability to handle announced and unannounced meals with meal uncertainties. Zone-MPC showed significant advantages over the "optimal" open-loop treatment. Moreover, the Zone-MPC reduces the control moves variability with minimal loss of performance comand the analyte monitoring system may be embodied as computer programs developed using an object oriented language that allows the modeling of complex systems. The software required to carry out the methods of the disclosure may be stored in the memory or storage device of the delivery device, the controller unit, the data terminal, and/or the analyte monitoring system and may include one or more computer program products.

A large number of various analyte measurement devices (e.g., glucose meters) and infusion pump systems are known in the art. For example, Diabetes Forecast puts out a yearly publication listing consumer measurement devices and pump systems. Any of these systems may include a controller or computer instructions to cause a sensor device or infusion systems to carry out the methods of the disclosure.

While various specific embodiments have been illustrated and described, it will be appreciated that various changes can be made without departing from the spirit and scope of the invention(s).

What is claimed is:

1. A zone model predictive control (MPC) method of continuous monitoring and delivery of an insulin or insulin analog to a subject comprising:

utilizing a linear difference model in combination with a model predictive control (MPC) algorithm to control delivery of the insulin or insulin analog within a zone of desired values, wherein the linear difference model and MPC algorithm are implemented, using sufficiently programmed computer, according to steps:

obtaining insulin and meal data values and continuous glucose monitoring (CGM) data values for the subject;

mapping the data using transfer functions:

$$I_{map}(s) = \frac{1}{(\tau_1 s + 1)(\tau_2 s + 1)} I(s)$$

$$M_{map}(s) = \frac{1}{(\tau_3 s + 1)(\tau_4 s + 1)} M(s)$$

generating a linear difference model comprising a plurality of states:

$$G_{k+1} = \alpha_1 G_k + \ldots + \alpha_p G_{k-p} +$$
$$\beta_{11} I_{map,k-d_1-1} + \ldots +$$
$$\beta_{1q_1} I_{map,k-d_1-q_1} + \ldots +$$
$$\beta_{21} M_{map,k-d_2-1} + \ldots + \beta_{2q_2} M_{map,k-d_2-q_2}$$

$$I_{map,k+1} = \gamma_1 I_{map,k} + \gamma_2 I_{map,k-1} + \gamma_3 I_k + \gamma_4 I_{k-1}$$

$$M_{map,k+1} = \delta_1 M_{map,k} + \delta_2 M_{map,k-1} + \delta_3 M_k + \delta_4 M_{k-1},$$

obtaining a defined glycemic zone for the subject;

calculating a next administration dose and/or time of delivery of the insulin or insulin analog based on a predicted glycemic value for the subject using the linear difference model and the defined glycemic zone; and delivering the insulin or insulin analog to the subject based upon the calculated next insulin administration, wherein:

I and M are insulin and meal data values expressed as amounts of insulin and carbohydrates, respectively, $I_{map}$ and $M_{map}$ are new states representing mapped insulin and meal values, respectively, $\tau_{1-4}$ are time points of measurement, s is a variable in unit of inverse time, G is glucose blood concentration, k is a time instant, $\alpha_1$, $\beta_{11}$, and $\beta_{21}$ are model coefficients, $d_1$ and $d_2$ are insulin and meal time delays, respectively, p, $q_1$, and $q_2$ are orders of glucose, insulin, and meal, respectively, and $\gamma_i$ and $\delta_i$ represent weighting factors for insulin and meal, respectively, after being absorbed into the blood.

2. The method of claim 1, wherein the next administration is performed by an insulin delivery pump or device.

3. The method of claim 1, wherein the next administration is performed by a computerized implanted insulin pump.

4. The method of claim 1, wherein the delivery of insulin varies temporally and by dose, the delivery of insulin is a continuous or discrete infusion, and the maximum glucose levels following each meal are maintained within the glycemic zone.

5. The method of claim 1, wherein the CGM data are episotic glucose measurements or self-monitoring measurements.

6. The method of claim 1, wherein the CGM data are sensor data, wherein the sensor is selected from an implanted glucose sensor, an optical glucose sensor, enzymatic glucose sensor and a finger stick glucose sensor.

7. The method of claim 1 wherein the Zone-MPC is based on linear difference equations initiated by an auto-regression with exogenous input (ARX) model selected by its prediction competency and then re-optimized to improve its prediction abilities.

8. The method of claim 1 wherein open loop data collection of insulin meals is obtained by feeding the subject followed by bolus injection of insulin.

9. The method of claim 1 wherein an automatic model identification formula is identified from a plurality of different autoregression exogenous (ARX) input models based upon the measured and mapped insulin meals and glucose measurements.

* * * * *